US010799117B2

(12) United States Patent
Sands et al.

(10) Patent No.: US 10,799,117 B2
(45) Date of Patent: Oct. 13, 2020

(54) PATIENT TREATMENT AND MONITORING SYSTEMS AND METHODS WITH CAUSE INFERENCING

(75) Inventors: Jeffrey J. Sands, Celebration, FL (US); Josè Diaz-Buxo, Charlotte, NC (US); Christian Schlaeper, Concord, CA (US); Martin Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 13/397,265

(22) Filed: Feb. 15, 2012

(65) Prior Publication Data

US 2013/0211206 A1 Aug. 15, 2013

Related U.S. Application Data

(63) Continuation-in-part of application No. 12/613,394, filed on Nov. 5, 2009, now Pat. No. 8,632,485.

(51) Int. Cl.
*G06F 19/00* (2018.01)
*G16H 20/13* (2018.01)
(Continued)

(52) U.S. Cl.
CPC .......... *A61B 5/0022* (2013.01); *A61B 5/4839* (2013.01); *A61M 1/14* (2013.01); *A61M 1/1605* (2014.02); *G06F 19/3481* (2013.01); *G16H 20/13* (2018.01); *A61B 5/021* (2013.01); *A61B 5/024* (2013.01); *A61B 5/026* (2013.01);
(Continued)

(58) Field of Classification Search
CPC .................................................. G06Q 50/22–24
See application file for complete search history.

(56) References Cited

U.S. PATENT DOCUMENTS 2,887,109 A 5/1959 Barrington
2,939,770 A 6/1960 Schwartzkopff
(Continued)

FOREIGN PATENT DOCUMENTS

DE 10049393 A1 4/2002
EP 1271386 A2 1/2003
(Continued)

OTHER PUBLICATIONS

Nintendo, "Wii Opertations Manual" 2011.*
(Continued)

*Primary Examiner* — Neal Sereboff
(74) *Attorney, Agent, or Firm* — Davis Malm & D'Agostine, P.C.; David J. Powsner

(57) ABSTRACT

The invention provides a health care delivery system comprising a plurality of health care delivery devices (e.g., via the Internet, etc.), which can disposed in treatment centers ranging from patient homes to commercial health care facilities such as hospitals, dialysis centers and so forth. Reporting functionality can, instead of or in addition to identifying (and reporting on) discrepancies in the raw and/or analyzed data from the delivery devices, infer (and report) on possible causes of those discrepancies and, in some aspects of the invention, remedy those causes, thereby, providing automated operations support for the treatment centers.

15 Claims, 7 Drawing Sheets

(51) Int. Cl.
*A61B 5/00* (2006.01)
*A61M 1/14* (2006.01)
*A61M 1/16* (2006.01)
A61B 5/0205 (2006.01)
A61B 5/145 (2006.01)
A61B 5/021 (2006.01)
A61B 5/1468 (2006.01)
A61B 5/024 (2006.01)
A61B 5/026 (2006.01)

(52) U.S. Cl.
CPC ......... *A61B 5/02055* (2013.01); *A61B 5/1468* (2013.01); *A61B 5/14542* (2013.01); *A61B 2505/07* (2013.01); *A61M 2205/18* (2013.01); *A61M 2205/3317* (2013.01); *A61M 2205/3324* (2013.01); *A61M 2205/3331* (2013.01); *A61M 2205/3334* (2013.01); *A61M 2205/3344* (2013.01); *A61M 2205/3368* (2013.01); *A61M 2205/3379* (2013.01); *A61M 2205/3553* (2013.01); *A61M 2205/3561* (2013.01); *A61M 2205/502* (2013.01); *A61M 2230/06* (2013.01); *A61M 2230/30* (2013.01); *A61M 2230/50* (2013.01)

(56) References Cited

U.S. PATENT DOCUMENTS

| | | | |
|---|---|---|---|
| 3,637,997 | A | 1/1972 | Petersen |
| 4,245,244 | A | 1/1981 | Lijewski et al. |
| 4,248,226 | A | 2/1981 | Pitchford, Jr. |
| 4,396,383 | A | 8/1983 | Hart |
| 4,614,267 | A | 9/1986 | Larkin |
| 4,737,036 | A | 4/1988 | Offermann |
| 4,936,446 | A | 6/1990 | Lataix |
| 5,185,597 | A | 2/1993 | Pappas et al. |
| 5,276,611 | A | 1/1994 | Ghiraldi |
| 5,283,560 | A | 2/1994 | Bartlett |
| 5,293,470 | A | 3/1994 | Birch et al. |
| 5,345,250 | A | 9/1994 | Inoue et al. |
| 5,367,316 | A | 11/1994 | Ikezaki |
| 5,389,947 | A | 2/1995 | Wood et al. |
| 5,396,281 | A | 3/1995 | Maeda |
| 5,401,238 | A | 3/1995 | Pirazzoli |
| 5,431,496 | A | 7/1995 | Balteau et al. |
| 5,434,626 | A | 7/1995 | Hayashi et al. |
| 5,781,442 | A | 7/1998 | Engleson et al. |
| 5,798,752 | A | 8/1998 | Buxton et al. |
| 5,825,352 | A | 10/1998 | Bisset et al. |
| 5,838,291 | A | 11/1998 | Ohshima et al. |
| 5,850,221 | A | 12/1998 | Macrae et al. |
| 5,858,239 | A | 1/1999 | Kenley et al. |
| 5,865,745 | A | 2/1999 | Schmitt et al. |
| 5,900,859 | A | 5/1999 | Takishita et al. |
| 5,903,211 | A | 5/1999 | Flego et al. |
| 5,933,136 | A | 8/1999 | Brown |
| 5,946,659 | A | 8/1999 | Lancelot et al. |
| 6,036,357 | A | 3/2000 | Van Drie |
| 6,057,826 | A | 5/2000 | Gaultier et al. |
| 6,118,430 | A | 9/2000 | Igari |
| 6,143,181 | A | 11/2000 | Falkvall et al. |
| 6,146,523 | A | 11/2000 | Kenley et al. |
| 6,151,581 | A | 11/2000 | Kraftson et al. |
| 6,335,725 | B1 | 1/2002 | Koh et al. |
| 6,335,761 | B1 | 1/2002 | Glen et al. |
| 6,359,631 | B2 | 3/2002 | DeLeeuw |
| 6,379,032 | B1 | 4/2002 | Sorensen |
| 6,462,786 | B1 | 10/2002 | Glen et al. |
| 6,469,695 | B1 | 10/2002 | White |
| 6,481,571 | B1 | 11/2002 | Kelders et al. |
| 6,493,002 | B1 | 12/2002 | Christensen |
| 6,493,747 | B2 | 12/2002 | Simmon et al. |
| 6,507,868 | B2 | 1/2003 | Simmon et al. |
| 6,574,503 | B2 | 6/2003 | Ferek-Petric |
| 6,684,379 | B2 | 1/2004 | Skoll et al. |
| 6,736,789 | B1 | 5/2004 | Spickermann |
| 6,738,052 | B1 | 5/2004 | Manke et al. |
| 6,746,398 | B2 | 6/2004 | Hervy et al. |
| 6,820,050 | B2 | 11/2004 | Simmon et al. |
| 6,912,664 | B2 | 6/2005 | Ranganathan et al. |
| 6,919,269 | B2 | 7/2005 | Schneegans et al. |
| 6,982,727 | B2 | 1/2006 | Baer et al. |
| 7,015,899 | B2 | 3/2006 | Kim |
| 7,038,588 | B2 | 5/2006 | Boone et al. |
| 7,044,927 | B2 | 5/2006 | Mueller et al. |
| 7,088,343 | B2 | 8/2006 | Smith et al. |
| 7,134,966 | B1 | 11/2006 | Tice |
| 7,154,397 | B2 | 12/2006 | Zerhusen et al. |
| 7,170,500 | B2 | 1/2007 | Canova, Jr. |
| 7,185,282 | B1 | 2/2007 | Naidoo et al. |
| 7,188,151 | B2 | 3/2007 | Kumar et al. |
| 7,190,352 | B2 | 3/2007 | Ling et al. |
| 7,215,991 | B2 | 5/2007 | Besson et al. |
| 7,284,262 | B1 | 10/2007 | Meric et al. |
| 7,336,187 | B2 | 2/2008 | Hubbard, Jr. et al. |
| 7,351,340 | B2 | 4/2008 | Connell et al. |
| 7,584,108 | B2 | 9/2009 | Brown |
| 7,627,334 | B2 | 12/2009 | Cohen et al. |
| 7,685,005 | B2 | 3/2010 | Riff et al. |
| 7,722,594 | B1 | 5/2010 | Frezza |
| 7,801,598 | B2 * | 9/2010 | Zhu .................. A61B 5/022 600/547 |
| 7,801,746 | B2 | 9/2010 | Moll et al. |
| 7,866,465 | B2 | 1/2011 | Dverin |
| 7,956,847 | B2 | 6/2011 | Christie |
| 8,100,770 | B2 * | 1/2012 | Yamazaki ........... A63F 13/06 463/39 |
| 8,182,440 | B2 | 5/2012 | Cruz et al. |
| 8,500,694 | B2 * | 8/2013 | Susi ............... A61M 5/14228 604/151 |
| 8,543,420 | B2 | 9/2013 | Darby et al. |
| 8,632,485 | B2 | 1/2014 | Schlaeper et al. |
| 8,698,741 | B1 | 4/2014 | Wang et al. |
| 8,970,503 | B2 | 3/2015 | Christie et al. |
| 8,974,414 | B2 | 3/2015 | Alisantoso et al. |
| 10,299,633 | B2 | 5/2019 | Shaw |
| 10,646,634 | B2 | 5/2020 | Yu et al. |
| 2001/0005115 | A1 | 6/2001 | Busio et al. |
| 2001/0011036 | A1 | 8/2001 | Miyamoto et al. |
| 2001/0016056 | A1 | 8/2001 | Westphal et al. |
| 2001/0034614 | A1 | 10/2001 | Fletcher-Haynes et al. |
| 2001/0045395 | A1 | 11/2001 | Kitaevich et al. |
| 2001/0050610 | A1 | 12/2001 | Gelston |
| 2001/0056226 | A1 | 12/2001 | Zodnik et al. |
| 2002/0032385 | A1 | 3/2002 | Raymond et al. |
| 2002/0035637 | A1 | 3/2002 | Simmon et al. |
| 2002/0082728 | A1 | 6/2002 | Mueller et al. |
| 2002/0107449 | A1 | 8/2002 | Roeher |
| 2002/0118595 | A1 | 8/2002 | Miller et al. |
| 2002/0163178 | A1 | 11/2002 | Williams |
| 2002/0198473 | A1 | 12/2002 | Kumar et al. |
| 2003/0001743 | A1 | 1/2003 | Menard |
| 2003/0018395 | A1 | 1/2003 | Crnkovich et al. |
| 2003/0069481 | A1 | 4/2003 | Hervy et al. |
| 2003/0083901 | A1 | 5/2003 | Bosch et al. |
| 2003/0135392 | A1 | 7/2003 | Vrijens et al. |
| 2003/0141981 | A1 | 7/2003 | Bui et al. |
| 2003/0150748 | A1 | 8/2003 | Crawley |
| 2003/0158508 | A1 | 8/2003 | DiGianfilippo et al. |
| 2003/0197690 | A1 | 10/2003 | Zimenkov |
| 2003/0198406 | A1 | 10/2003 | Bibbo et al. |
| 2003/0218935 | A1 | 11/2003 | Hu |
| 2003/0220607 | A1 | 11/2003 | Busby et al. |
| 2004/0021673 | A1 | 2/2004 | Alessi et al. |
| 2004/0027912 | A1 | 2/2004 | Bibbo et al. |
| 2004/0047232 | A1 | 3/2004 | Terentiev |
| 2004/0104250 | A1 | 6/2004 | Rousselet |
| 2004/0111293 | A1 | 6/2004 | Firanek et al. |
| 2004/0111294 | A1 | 6/2004 | McNally et al. |
| 2004/0128162 | A1 | 7/2004 | Schlotterbeck et al. |
| 2004/0167804 | A1 | 8/2004 | Simpson et al. |
| 2004/0176984 | A1 | 9/2004 | White et al. |
| 2004/0193448 | A1 | 9/2004 | Woodbridge et al. |

(56) References Cited

U.S. PATENT DOCUMENTS

| | | |
|---|---|---|
| 2004/0195264 A1 | 10/2004 | Mastbrook |
| 2004/0220832 A1 | 11/2004 | Moll et al. |
| 2004/0260478 A1 | 12/2004 | Schwamm |
| 2004/0261037 A1 | 12/2004 | Ording et al. |
| 2005/0021369 A1 | 1/2005 | Cohen et al. |
| 2005/0055242 A1* | 3/2005 | Bello .................. G16H 40/67 705/2 |
| 2005/0059163 A1 | 3/2005 | Dastane et al. |
| 2005/0073908 A1 | 4/2005 | Bibbo et al. |
| 2005/0081164 A1 | 4/2005 | Hama et al. |
| 2005/0092373 A1 | 5/2005 | Schafer et al. |
| 2005/0108057 A1 | 5/2005 | Cohen et al. |
| 2005/0144044 A1 | 6/2005 | Godschall et al. |
| 2005/0201345 A1 | 9/2005 | Williamson |
| 2006/0010400 A1 | 1/2006 | Dehlin et al. |
| 2006/0047538 A1 | 3/2006 | Condurso et al. |
| 2006/0058603 A1 | 3/2006 | Dave et al. |
| 2006/0062238 A1 | 3/2006 | Mahendran et al. |
| 2006/0066581 A1 | 3/2006 | Lyon et al. |
| 2006/0100530 A1* | 5/2006 | Kliot .................. A61B 5/08 600/483 |
| 2006/0176403 A1 | 8/2006 | Gritton et al. |
| 2006/0190297 A1 | 8/2006 | Glass et al. |
| 2006/0231108 A1 | 10/2006 | Novatzky et al. |
| 2007/0040787 A1 | 2/2007 | Saha |
| 2007/0046596 A1 | 3/2007 | Sakakibara et al. |
| 2007/0078878 A1 | 4/2007 | Knable |
| 2007/0091716 A1 | 4/2007 | Zeikus |
| 2007/0112603 A1* | 5/2007 | Kauthen ............ G06F 19/3481 705/3 |
| 2007/0125709 A1 | 6/2007 | Nigam |
| 2007/0130287 A1 | 6/2007 | Kumar et al. |
| 2007/0168229 A1 | 7/2007 | Kim |
| 2007/0223877 A1 | 9/2007 | Kuno |
| 2007/0251336 A1 | 11/2007 | Nielsen et al. |
| 2008/0027374 A1 | 1/2008 | Jensen et al. |
| 2008/0097283 A1 | 4/2008 | Plahey |
| 2008/0097550 A1 | 4/2008 | Dicks et al. |
| 2008/0154177 A1 | 6/2008 | Moubayed et al. |
| 2008/0171596 A1* | 7/2008 | Hsu .................. A63F 13/212 463/39 |
| 2008/0268413 A1 | 10/2008 | Leichner |
| 2008/0275721 A1 | 11/2008 | Nagai et al. |
| 2008/0294019 A1* | 11/2008 | Tran .................. A61B 5/04005 600/301 |
| 2009/0008331 A1 | 1/2009 | Wilt et al. |
| 2009/0037216 A1 | 2/2009 | Bluemler et al. |
| 2009/0076338 A1 | 3/2009 | Zdeblick et al. |
| 2009/0076856 A1* | 3/2009 | Darby .................. G09B 23/28 705/3 |
| 2009/0306573 A1 | 12/2009 | Gagner et al. |
| 2010/0010428 A1 | 1/2010 | Yu et al. |
| 2010/0076398 A1* | 3/2010 | Scheurer ............ A61B 5/0215 604/505 |
| 2010/0137693 A1 | 6/2010 | Porras et al. |
| 2010/0302897 A1 | 12/2010 | George et al. |
| 2010/0317602 A1* | 12/2010 | Moore .................. A61K 31/198 514/23 |
| 2011/0105979 A1 | 5/2011 | Schlaeper et al. |
| 2012/0277170 A1* | 11/2012 | Moore .................. A61K 31/405 514/23 |
| 2014/0298171 A1 | 10/2014 | Wang et al. |
| 2018/0369806 A1 | 12/2018 | Behnk |

FOREIGN PATENT DOCUMENTS

| | | | |
|---|---|---|---|
| EP | 2043014 | * 1/2009 | .......... 705/3 |
| EP | 2043014 A1 | 4/2009 | |
| JP | 2003006331 A | 1/2003 | |
| JP | 2008284229 A | 11/2008 | |
| KR | 2001-091801 A | 10/2001 | |
| WO | 96/28086 A1 | 9/1996 | |
| WO | 0207591 | 1/2002 | |
| WO | 2004070995 A2 | 8/2004 | |
| WO | 2006018555 A1 | 2/2006 | |
| WO | 2006020862 A2 | 2/2006 | |
| WO | 2006/122325 A2 | 11/2006 | |
| WO | 2007/035696 A1 | 3/2007 | |
| WO | 2007033600 A1 | 3/2007 | |
| WO | 2007/038147 A2 | 4/2007 | |
| WO | 2007/040963 A2 | 4/2007 | |
| WO | 2007/040975 A2 | 4/2007 | |
| WO | 2007/044877 A2 | 4/2007 | |
| WO | 2007/049163 A2 | 5/2007 | |
| WO | 2007/053683 A2 | 5/2007 | |
| WO | 2007049253 A2 | 5/2007 | |
| WO | 2007120904 A2 | 10/2007 | |
| WO | 2007126360 A1 | 11/2007 | |
| WO | 2008008281 A2 | 1/2008 | |
| WO | 2008110674 A1 | 9/2008 | |
| WO | 2009002620 A1 | 12/2008 | |

OTHER PUBLICATIONS

Fresenius Medical Care, "Dialysis Products" 2008.*
Cowling et al., "Hypotension in the PACU: An Algorithmic Approach" 2002 Journal of PeriAnesthesia Nursing vol. 17, No. 3.*
US NIH, "MedlinePlus—Hypotension" updated Feb. 20, 2011.*
Schneider, Jon "Jon Schneider's Tech Blog" Feb. 8, 2009.*
Bausch et al. "Physiological responses while playing Nintendo Wii Sports" Journal of Undergraduate Kinesiology Research May 2, 2008, vol. 3.*
Hansen, Susan "Dialysis Procedures—Initiation, Monitoring, Discontinuing" NANT $26^{th}$ Annual National Symposium, Feb. 10-12, 2009.*
[No Author] Dialysis data acquisition and management system: Finesse® Professional. Fresenius Medical Care. Product information sheet. 2002, 2 pages.
[No Author] Dialysis data management system FinProDB: Finesse® Professional Database. Fresenius Medical Care. Product information sheet. 2004, 2 pages.
[No Author] Exalis: Dialysis data management tool. Gambro Lundia AB. Product information sheet. Jun. 2002, 8 pages.
[No Author] Finesse®. Fresenius Medical Care. Retrieved Jun. 17, 2009 from http://fmc.intra.fresenius.de. 2008, 2 pages.
[No Author] Finesse® HomeHemo Dialysis (TI 1025 e, v2.01). Medvision AG. Product information sheet. 2004, 6 pages.
[No Author] Therapy Data Management System: Data acquisition, data management and quality assurance as an integrated solution. Fresenius Medical Care. Product information sheet. 2007, 12 pages.
Anonymous: "Interactive Hospital Menus Go Prime Time" Internet Article. Dietary Manager Magazine, [Online] Apr. 2007 (Apr. 2007), pp. 29-31, XP002505453 Retrieved from the Internet: URL:http://www.dmaonline.org/Publications/ articles/2007-04-Interactive.pdf> [retrieved on Nov. 25, 2008].
Anonymous: "PatientLife:)System TM ?your comprehensive solution for patient-centered care" Internet Article. Brochure. Getwellnetwork, Inc., [Online] Mar. 18, 2006 (Mar. 18, 2006), pp. 1-6, XP002505452 Retrieved from the Internet: URL:http://web.archive.org/web/20060318175 409/http://www.getwellnetwork.com/pdfs/GWN ProductBrochure.pdf> [retrieved on Nov. 25, 2008].
European Search Report, EP 08 164 694.7, dated Oct. 12, 2008.
Intel 510k Summary, Jun. 27, 2008.
Nakamoto, Telemedicine System for Patients on Continuous Ambulatory Peritoneal Dialysis, Peritoneal Dialysis International, vol. 27, 2007.
NHS Lothian Implements Intels Personal Health System to Manage Patients with Chronic Conditions, Intel, Feb. 24, 2009.
International Search Report dated Jul. 23, 2007, for Application No. PCT/US2006/42650 (11 Pages).
[No Author Listed] Nintendo, "Wii Fit Plus" 34 pages. 2009.

* cited by examiner

Figure 4

| Treatment Center | # patients | # tx | %Tx with Hypotension | alarms/Tx | alarm min/ Tx | Alarm min/ alarm |
|---|---|---|---|---|---|---|
| 1 | 59 | 2127 | 24.4% | 2.88 | 2.79 | 0.97 |
| 2 | 133 | 3730 | 18.7% | 4.13 | 3.78 | 0.92 |
| 3 | 92 | 1789 | 20.6% | 2.49 | 2.33 | 0.94 |
| 4 | 86 | 1328 | 14.0% | 2.47 | 2.17 | 0.88 |
| 5 | 55 | 480 | 27.9% | 5.91 | 5.46 | 0.92 |
| 6 | 65 | 466 | 23.0% | 2.90 | 2.95 | 1.01 |
| 7 | 55 | 562 | 19.8% | 2.54 | 2.17 | 0.85 |
| 8 | 177 | 954 | 8.8% | 3.27 | 2.84 | 0.87 |
| Total | 722 | 11436 | 19.3% | 3.31 | 3.05 | 0.92 |

Figure 6

PATIENT TREATMENT AND MONITORING SYSTEMS AND METHODS WITH CAUSE INFERENCING

This application is a continuation-in-part of U.S. patent application Ser. No. 12/613,394, filed Nov. 5, 2009, entitled "Patient Treatment and Monitoring Systems and Methods," the teachings of which are incorporated herein by reference

BACKGROUND OF THE INVENTION

The invention relates to apparatus and methods for medical treatment. It has application, by way of non-limiting example, in the delivery of dialysis care, e.g., in the home, in hospitals, dialysis centers or other central care facilities.

Dialysis is an important treatment regimen for a variety of chronic diseases. To meet the need for regular care, patients typically travel to hospitals or dialysis centers that are designed for efficient and routine therapy. Typically, a nurse or patient care technician oversees the treatment sessions and records patient information, such as patient vitals, treatment details, and billing information. The nurse or care technician can also assess the patient's health and, if necessary, make a referral to his or her regular physician (or, if necessary, to an emergency physician) for additional medical attention.

With the advent of more affordable equipment, home dialysis is increasingly an option for many dialysis patients, who find it offers them greater privacy, flexibility of scheduling and overall comfort. Home provision of hemodialysis can also be advantageous to health care providers since it does not require the nursing, equipment and space overhead of standard in-center care. Medicare/Medicaid and other insurers stand to benefit, too, since home hemodialysis tends to lower coverage costs over the long term.

The decision to place a patient on home hemodialysis (HHD) is not necessarily an easy one, however. The demands of a hemodialysis regime, even one administered in the home, are such that HHD programs suffer a high dropout rate as patients revert to in-center dialysis. These dropouts are not necessarily for medical reasons but, rather, are often due to the mental and/or physical demands HHD care places on patients and their partners. Considering the costs of providing patient training, the expenses of adjustment of the infrastructure at the patient's home, cost for installation of the equipment and delivery charges, patients that drop out of HHD programs create an economic burden on the health care system.

Even for those patients on a course of HHD therapy, full compliance with the regimen can be difficult. This is true, for example, with respect to administration of medications taken as part of the regimen. Erythropoietin, a drug commonly administered to hemodialysis patients to prevent anemia, is one example. Dosages of this expensive drug can be reduced, if it administered subcutaneously. That can be more painful, however, leading HHD patients to skip doses. This not only adversely affects treatment outcome but may raise the specter of insurance fraud—since, unless the patients admit they are under-dosing, care providers are likely to dispense and seek reimbursement for monthly complements of EPO, regardless of whether patients have used them.

An additional consideration in the decision to place a patient on HHD is that of patient monitoring. HHD therapy affords fewer opportunities to assess patient health, well-being and treatment compliance. Care givers typically have that opportunity only when HHD patients visit their local dialysis clinic for monthly evaluation—and, then, only to the extent that the success of treatment can be determined from routine testing and from patient reporting. Significantly, although HHD equipment may record limited patient information (such as date/time of treatment, blood pressure and pulse), it does not afford the care giver insight into adverse events that occur during actual HHD treatment sessions, such as dizziness, vomiting and cramps. Moreover, while the prior art does suggest that there has been some effort to collect in a central databases even the limited patient data acquired by HHD equipment, this has not been perceived by care providers as a suitable substitute for in-center visits.

In view of the foregoing an object of the invention is to provide improved medical care systems and methods. A more particular object is to provide such systems and methods as are adapted for patient treatment and monitoring.

A further object of the invention is to provide such systems and methods as are adapted for use in health delivery, e.g., in the home, in hospitals, dialysis centers or other central care facilities.

A still further object of the invention is to provide such systems and methods as are adapted for use in hemodialysis and peritoneal dialysis treatment.

A still further object of the invention is to provide such systems and methods as are adapted for use in hemodialysis and peritoneal dialysis treatment, regardless of the treatment setting (e.g., whether operated at a central care facility, a home or otherwise).

SUMMARY OF THE INVENTION

The foregoing are among the objects attained by the invention, which provides apparatus and methods for delivery of health care that collect subjective and objective measures of patient health and treatment, analyzing them (e.g., correlating them with one another, with prior such information and/or with norms) and reporting them to aid in on-going patient diagnosis and treatment (both on acute and chronic bases), as well as to aid physicians, nurses and other caregivers in decision support, monitoring treatment compliance, facilitating regulatory compliance, billing, and so forth. Advantages of the system are, among others, that it helps ensure that the patient is doing as expected (e.g., in terms of physical health, mental health and well-being, and/or treatment compliance), allowing care providers to readily monitor and document (or otherwise report on) the patient's treatment and response, providing alerts or other warnings when those are not proceeding as expected.

Thus, for example, in some aspects, the invention provides a health care delivery device comprising a medical treatment apparatus, such as a hemodialysis or peritoneal dialysis unit, that is coupled to a processor. The processor generates patient queries in connection with treatments rendered by dialysis equipment (or other treatment apparatus). The queries are directed, at least in part, to subjective topics, such as the state of the patient's mental health and well being, quality of life, degrees of pain, views on success of therapy, and so forth. They are presented on an LCD screen or other output device coupled to the processor to elicit responses on a keyboard or other input device, also coupled to the processor.

Further aspects of the invention provide a health care delivery device, for example, as described above, that includes communications logic, e.g., hardware and/or software operating in conjunction with the processor, that transmits the patient's query responses to a health care provider, e.g., a nurse or patient care technician at a dialysis center.

Those responses can be transmitted in connection with treatments rendered by the dialysis equipment (or other treatment apparatus), e.g., at or around the time of completion of each treatment session.

In related aspects of the invention, a health care delivery device, for example, as described above, can include a memory or other store for patient responses. That store can operate in connection with the communications logic, e.g., retaining the responses while awaiting transmission to the health care provider.

Further aspects of the invention provide a health care delivery device, for example, as described above, wherein the communications logic transmits text or other messages input by the patient (e.g., via the input device) to the health care provider. The messages can be, for example, questions by the patient regarding his or her immediate or long-term treatment. In related aspects of the invention, the communications logic of such a health care delivery device can accept messages transmitted from the provider and can present those messages on the output device. These can be, for example, responses to the patient's questions, suggestions on treatment, words of encouragement, and so forth.

Still further aspects of the invention provide a health care delivery device, for example, as described above, that includes one or more physiometric sensors that take readings, e.g., of patient temperature, blood pressure, other vital signs, and so forth, in connection with treatments rendered by the dialysis equipment (or other treatment apparatus). The communications logic can transmit those readings to the health care provider, e.g., along with the patient's responses to the queries for the corresponding treatment session.

In related aspects of the invention, a health care delivery device, for example, as described above, includes one or more sensors that sense operating conditions of any of the health device and the medical treatment apparatus. The communications logic can transmit those readings to the health care provider, e.g., along with the patient's responses to the queries and/or physiometric readings for the corresponding treatment session.

In further related aspects of the invention, a health care delivery device, for example, as described above, includes one or more one or more monitors that signal alerts or alarms (terms which are used interchangeably herein) in response to any of (i) selected patient physiometric characteristics, e.g., pulse, blood pressure and/or other vital sign readings over designated values, etc., and (ii) selected operating conditions of any of the health device and the medical treatment apparatus, e.g., diagnostic warnings, power surges, and so forth. As above, the communications logic can transmit those alerts to the health care provider, e.g., along with the patient's responses and/or physiometric readings.

Still other aspects of the invention provide a health care delivery system that includes a health care delivery device, for example, as described above, that is coupled to a digital data processing system, e.g., by way of the Internet, a cellular phone network, or other arrangement of wireless and/or wired network media. In a system according to this aspect of the invention, the health care delivery device can be disposed, for example, in a patient's home and the digital data processing system can be disposed, for example, in a hospital, dialysis center or other central location. The communication system, according to these aspects of the invention, transmits patient responses, physiometric readings, operating conditions and/or alerts to the remote digital data processing system, e.g., in connection with treatments rendered by the dialysis equipment (or other treatment apparatus) or otherwise.

In related aspects of the invention, the digital data processing system of a health care delivery system, e.g., as described above, analyzes patient responses, physiometric readings, operating conditions and/or alerts received from the health care delivery device and, for example, correlates them with (i) each other, (ii) prior responses, readings, conditions, alerts from the device and/or other information for the patient (e.g., from medical records), (iii) expected responses, readings, conditions and/or alerts, e.g., based on empirical, normative or other standards, and/or (iv) so forth, in order to aid the health care provider in on-going patient diagnosis and treatment (both on acute and chronic bases), decision support, monitoring treatment compliance, facilitating regulatory compliance, billing, and so forth.

In other related aspects of the invention, the digital data processing system of a health care delivery system, e.g., as described above, includes reporting functionality that reports patient responses, physiometric readings, operating conditions and/or alerts received from the health care delivery device. These can be on a per-session basis or over selected periods of time, e.g., per day, per week, etc. Alternatively and/or in addition, this functionality can report results of the aforementioned correlation(s), e.g., indicating whether the responses, readings, conditions and/or alerts show unexpected and/or undesirable indications.

By way of non-limiting example, the reporting functionality can report treatment times, medication dosages and times, alarms, and so forth. This can be used by the health care provider in providing acute and/or chronic care. It can be used, alternatively or in addition, for regulatory, billing or other such purposes. Selected portions of these reports, for example, can be automatically transmitted to the physician, nurse and other caregivers, as well as, for example, to the patient (e.g., via e-mail, messaging transmitted from the digital data processor to the health care delivery device, etc.), the insurer and/or others.

In other aspects of the invention, one or more of the aforementioned functions of the digital data processor can be carried out, instead or in addition, by the health care delivery device. Thus, for example, the processor executing on that device can analyze patient responses, physiometric readings, operating conditions and/or alerts and correlate them with (i) each other, (ii) prior responses, readings, conditions, alerts from the device and/or other information for the patient (e.g., from medical records), (iii) expected responses, readings, conditions and/or alerts, e.g., based on empirical, normative or other standards, and/or (iv) so forth. While the results of such analysis can be transmitted to the remote digital data processing system, e.g., for reporting to the health care provider, those results can be also be used to generate more urgent messages to the patient and/or his health care provider.

Other aspects of the invention provide a health care delivery system as described above in which the health care delivery device and the digital data processing system are located at the same facility (e.g., in a hospital, dialysis center or other central location) and/or in the same department, floor, ward and/or room of such a facility.

Further aspects of the invention provide a health care delivery system, e.g., as described above in which the digital data processing system is coupled to a plurality of the health care delivery devices (e.g., via the Internet, etc.), which can be disposed in treatment centers ranging from patient homes to commercial health care facilities such as hospitals, dialysis centers and so forth. The aforesaid reporting functionality can, instead of or in addition to identifying (and reporting on) discrepancies in the raw and/or analyzed data from the delivery devices, infer (and report) on possible causes of those discrepancies and, in some aspects of the invention, remedy those causes, thereby, providing automated operations support for the treatment centers. This may be based on, for example, patient heart rate, blood pressure, temperature, oxygen (O2) saturation, blood volume, blood flow, dialysate flow, conductivity, dialyzer clearance, alarm state, venous pressure, arterial pressure, and/or other information regarding the patients and/or the health care delivery devices, as provided by the aforementioned sensors or otherwise.

Related aspects of the invention provide health care delivery systems, e.g., as described above, in which the reporting functionality facilitates correction of the identified causes, e.g., the setting or resetting of alarms, recalibration of sensors, blocking or unblocking device operation, communicating or implementing a physician-ordered prescription, and so forth, all by way of example.

Related aspects of the invention provide health care delivery systems, e.g., as described above, in which the reporting functionality facilitates such correction indirectly, e.g., through alerting of (and action by) a technician or other personnel local to a device requiring such correction.

Further related aspects of the invention provide health care delivery systems, e.g., as described above, in which the reporting functionality facilitates such correction directly, e.g., by sending control signals to one or more of the health care delivery devices.

Still further related aspects of the invention provide health care delivery systems, e.g., as described above, in which the reporting functionality (i) infers from patterns of hypotension reflected in data from the health care delivery devices that patients under care at one or more treatment centers may require "dry weight" adjustment or other intervention, and (ii) generates reports and/or immediate alerts directing health care providers of such need for possible adjustment and/or effects such adjustment directly.

Yet further related aspects of the invention provide health care delivery systems, e.g., as described above, in which the reporting functionality makes such an inference whenever the sensors of a treating device detect an instance of hypotension during a treatment session. In other aspects, this can be conditioned on detection of multiple such instances during a session. In yet other aspects, it can be conditioned on detection of such condition or conditions over multiple treatment sessions of the same patient.

Still yet further related aspects of the invention provide health care delivery systems, e.g., as described above, in which the reporting functionality makes such an inference by cross-correlating hypotension alerts signaled (and/or blood pressure readings taken) by devices of one or more centers with treatment, administrative or other data from those devices and/or center(s). This can facilitate, for example, identification of a specific health care provider (e.g., dialysis nurse and/or physician) or group of providers (e.g., personnel of a given center, personnel trained by a specific trainer, and so forth) whose treatment regiments necessitate dry weight or other therapy adjustments.

Yet still yet other related aspects of the invention provide health care delivery systems, e.g., as described above, in which the reporting functionality infers, from like data as discussed above, that sensors of one or more devices may be signaling false hypotension alerts and/or providing incorrect blood pressure readings.

Related aspects of the invention provide health care delivery systems, e.g., as described above, in which the reporting functionality (i) infers from patterns of hypotension reflected in data from the health care delivery devices, as well, optionally, as from supplemental infusate supplies, sensors and/or monitoring logic of those devices that patients under care at one or more treatment centers may require medication adjustment, and (ii) generates reports and/or immediate alerts directing health care providers of the need for possible adjustments and/or effects such adjustment directly.

Related aspects of the invention provide health care delivery systems, e.g., as described above, in which the reporting functionality (i) infers from patterns of hypotension reflected in data from the health care delivery devices, as well, optionally, as from other sensors and/or monitoring logic of those devices that one or more of those devices may require filtration rate adjustment, and (ii) generates reports and/or immediate alerts directing health care providers of the need for such possible adjustment and/or effects such adjustment directly.

Related aspects of the invention provide health care delivery systems, e.g., as described above, in which the reporting functionality (i) infers from patterns of hypotension reflected in data from the health care delivery devices, as well, optionally, as from other sensors and/or monitoring logic of those devices that patients under care at one or more treatment centers may incoming/fresh dialysate temperature adjustment, and (ii) generates reports and/or immediate alerts directing health care providers of the need for such possible adjustment and/or effects such adjustment directly.

Related aspects of the invention provide health care delivery systems, e.g., as described above, in which the reporting functionality (i) infers from patterns of atrial and/or venus pressure alarms reflected in data from the health care delivery devices, as well, optionally, as from other sensors and/or monitoring logic of those devices that patients under care at one or more treatment centers may require hemocoagulant adjustment and/or vascular access evaluation, and (ii) generates reports and/or immediate alerts directing health care providers of the need for such possible adjustment and/or effects such adjustment directly.

Related aspects of the invention provide health care delivery systems, e.g., as described above, in which the reporting functionality (i) infers from patterns of conductivity alerts reflected in data from the health care delivery devices, as well, optionally, as from information from other sensors and/or monitoring logic of those devices that one or more of those devices may require supply correction, and (ii) generates reports and/or immediate alerts directing health care providers of the need for possible adjustments and/or effects such adjustment directly.

Related aspects of the invention provide health care delivery systems, e.g., as described above, in which the reporting functionality (i) infers from patterns of alerts, alarms and other information from the health care delivery devices indicative of dialysate temperature, dialysate flow, and so forth, that one or more of those devices may require supply correction, and (ii) generates reports and/or immediate alerts directing health care providers of the need for possible adjustments and/or effects such adjustment directly.

Still further aspects of the invention provide methods paralleling operation of the health care device, system, and components thereof, discussed above. By way of non-limiting example, one such method includes delivering medical treatment to a patient via a medical treatment apparatus, subjectively querying the patient via a health care treatment device associated with the medical treatment apparatus, accepting patient responses to those subjective queries, and transmitting the patient responses to a remote health care provider.

These and other aspects of the invention are evident in the drawings and in the text that follows.

BRIEF DESCRIPTION OF THE DRAWINGS

A more complete understanding of the invention may be attained by reference to the drawings, in which:

FIGS. 3-4 depict examples of reports of the type generated by a health care delivery system of FIG. 1;

FIG. 6 depicts a chart-style report of the type generated by an analysis and reporting module in a system of the type shown in FIG. 5 showing comparative treatment data for multiple commercial health care facilities.

DETAILED DESCRIPTION OF THE ILLUSTRATED EMBODIMENT

Architecture

Figure 1:
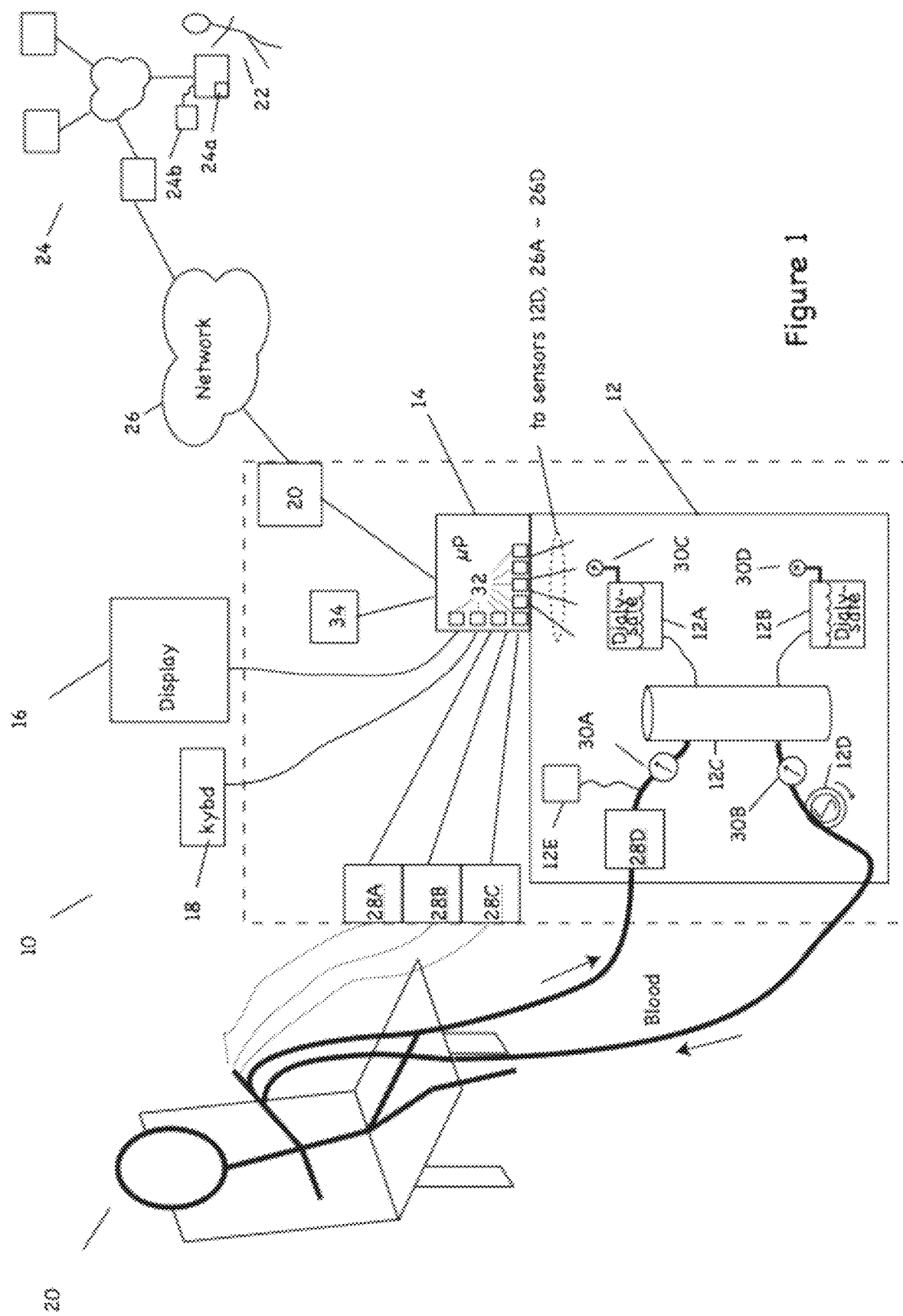
FIG. 1 depicts examples of a health care delivery device and system according to the invention.

FIG. 1 depicts examples of a health care delivery device and system according to the invention. Illustrated device 10 comprises a medical treatment apparatus 12, a processor 14, an output device 16 and an input device 18, all coupled as shown.

Illustrated medical treatment apparatus comprises a dialysis unit and, more particularly, a hemodialysis unit of the type commercially available or otherwise known in the art for such purpose, e.g., including, for example, fresh and spent dialysate containers 12A, 12B, filter/dialyzer 12C, pump 12D, supplemental infusate supply 12E (e.g., for heparin and/or other medications), and so forth, as adapted in accord with the teachings hereof. The illustrated medical treatment apparatus 12 is, moreover, of the type adapted for use in the home or other locale remote for a dialysis center, hospital or other central treatment center. Alternatively, or in addition, the apparatus 12 may be adapted for use in such a dialysis center, hospital or other treatment center. This may, for example, at a location in such a center remote from a physician, nurse, patient care technician or other health care provider—or it may be nearby such a provider. In other embodiments apparatus 12 may comprise a peritoneal dialysis machine or other medical treatment apparatus of the type known in the art or otherwise, again, as adapted in accord with the teachings hereof.

Processor 14 comprises a microprocessor or other processing unit of type commercially available or otherwise known in the art, as adapted in accord with the teachings hereof. The processor 14 may be integral to medical treatment apparatus 12 or it may separate therefrom, albeit coupled for communication therewith. Illustrated processor 14 is coupled with liquid crystal display (LCD) or other output device 16, which may be of the type commercially available in the marketplace or otherwise known in the art, as adapted in accord with the teachings hereof. Processor 14 is also coupled with keyboard or other input device 18 (e.g., mouse, touch-screen, touchpad, etc.) which, too, may be of the type commercially available in the marketplace or otherwise known in the art, again, as adapted in accord with the teachings hereof. The LCD 16 (and/or other output device) and/or keyboard 18 (and/or other input device) may be integral to medical treatment apparatus 12 or separate therefrom. Alternatively, or in addition, LCD 16 and/or keyboard 18 may be co-housed with processor 14 or separate therefrom, as well as from one another.

Processor 14 is coupled with network interface 20 to support communications with a health care provider 22, e.g., a physician, nurse or patient care technician, via digital data processing system 24 and network media 26. That media 26 may comprise IP, telephone and/or other networks of the type known in the art—wired, wireless and/or otherwise. Network interface 20 comprises a modem, network interface card and/or other functionality of the type commercially available in the marketplace or otherwise known in the art suitable for supporting communications over network 26, as adapted in accord with the teachings hereof. Examples include cable modems, cellular telephone modems, USB modems, Ethernet cards, and combinations thereof, just to name a few. It will be appreciated that some of that functionality for supporting communications with care provider 22 via digital data processor 24 and network media 26 may reside on processor 14, as in the case, for example, of operating system drivers, network protocol stacks, and so forth. Together, this functionality (i.e., hardware and/or software) is referred to, here, as "communications logic."

Processor 14 is also coupled with sensors 28 that take biometric readings of the patient 20. These "physiometric sensors," as they are referred to herein, can include blood pressure sensors, temperature sensors, and so forth. In the illustrated embodiment they are of the type commercially available in the marketplace or otherwise known in the art, as adapted in accord with the teachings hereof. Those sensors may be integral to apparatus 12, processor 14 and/or co-housed with device 10, or otherwise. In the illustrated embodiment, the sensors include a pulse sensor 28A, a blood pressure sensor 28B, a temperature sensor 28C and a electrochemical sensor 28D (e.g., for sensing blood urea levels, ammonia levels, and so forth). Sensors 28A—28C are shown coupled to the patient, while sensor 28D is coupled in the blood fluid-flow path of apparatus 12. Other embodiments of the invention may include a greater or fewer number of such sensors, coupled to the patient, the flow-path of apparatus 12, etc., as shown or in other ways known in the art, as adapted in accord with the teachings hereof.

Processor 14 is also coupled to sensors 30 that sense operating conditions of the device 10, apparatus 12, and/or components thereof. These can include sensors that measure the rates of fluid flow, fluid temperature, level, and composition, power conditions, maintenance status and so forth, all by way of non-limiting example. In the illustrated embodiment they are of the type commercially available in the marketplace or otherwise known in the art, as adapted in accord with the teachings hereof. Those sensors may be integral to apparatus 12, processor 14 and/or co-housed with device 10, or otherwise. In the illustrated embodiment, the sensors include an inflow blood flow-rate or pressure sensor 30A, and outflow blood flow-rate or pressure sensor 30B, fresh dialysate level sensor 30C, spent dialysate level sensor 30D. An additional sensor (not shown) can, by way of non-limiting example, sense levels or dosings from supplemental infusate supply 12E. In other embodiments, other operational sensors of the type suggested above are provided instead or in addition to those shown in the drawing and/or discussed here.

Processor 14 can include monitoring logic, here, represented by modules 32, that monitor operational states of device 10 and/or apparatus 12, as well as detect alert or alarm (terms which are used interchangeably herein) conditions, e.g., as reported directly from components of device 10 and/or apparatus 12 and/or when readings from the physiometric sensors 28 and/or operational sensors 32 fall outside of selected ranges. That monitoring logic can also, by way of non-limiting example, monitor when and for how long the various sensor readings, for example, are outside those ranges.

Thus, for example, the monitoring logic 32 can detect the incidence and duration of systolic blood pressure readings below physician- (or other care provider-) defined levels, as well as changes (deltas) in blood pressure greater than such levels. By way of further example, the monitoring logic can detect when medications are administered and in what quantity. By way of still further example, the monitoring logic can detect when treatment sessions are initiated and how long they are run; the incidence and duration of "door ajar" alerts, "filter replacement" alerts, "dialysate replacement" alerts, and/or other alerts or conditions reflecting whether proper and efficient care is being delivered to the patient 20, and so forth. Though illustrated here has modules (i.e., software and/or hardware) executing on/forming part of processor 14, in other embodiments, monitoring logic 32 can be form part of apparatus 12 and/or may be co-housed with device 10, or otherwise.

Processor 14 is also coupled, in the illustrated embodiment, with a storage device 34, such as a disk drive, memory stick and/or other medium, removable or otherwise.

Digital data processing system 24 comprises one or more cell phones, smart phones, personal digital assistants, computers, or other devices suitable for communicating with device 10 via network 26 to receive patient query responses, physiometric sensor readings, operational sensor readings and/or alerts of the type described above. In the illustrated embodiment, the system 24 is remote from device 10 and comprises a computer system of the type commonly available in a hospital, dialysis center or other central location of the type that employs or otherwise physicians, nurses, patient care technicians or other health care providers to oversee treatment of patients 20, all as adapted in accord with the teachings hereof. In other embodiments, the system 24 is located with the device 10 at the same facility (e.g., in a hospital, dialysis center or other central location) and/or in the same department, floor, ward and/or room of such a facility, by way of non-limiting example, and coupled therewith by way of a bus, network or other media, or combination thereof, wired or wireless, dedicated, shared or otherwise.

The illustrated system 24 also includes an analysis/reporting module 24A, implemented in software on one or more of the computers or other computational devices making up that system, that analyzes and/or reports the information collected and transmitted by device 10 in accord with the teachings hereof to aid in on-going patient diagnosis and treatment, as well as to aid physicians, nurses and other caregivers in diagnostics, decision support, monitoring treatment compliance, billing, and so forth. The system 24 also includes an LCD display or other output unit 24B of the type commercially available in the marketplace or otherwise known in the art (as adapted in accord with the teachings hereof) for presenting results generated by module 24A.

Operation

Figure 2:
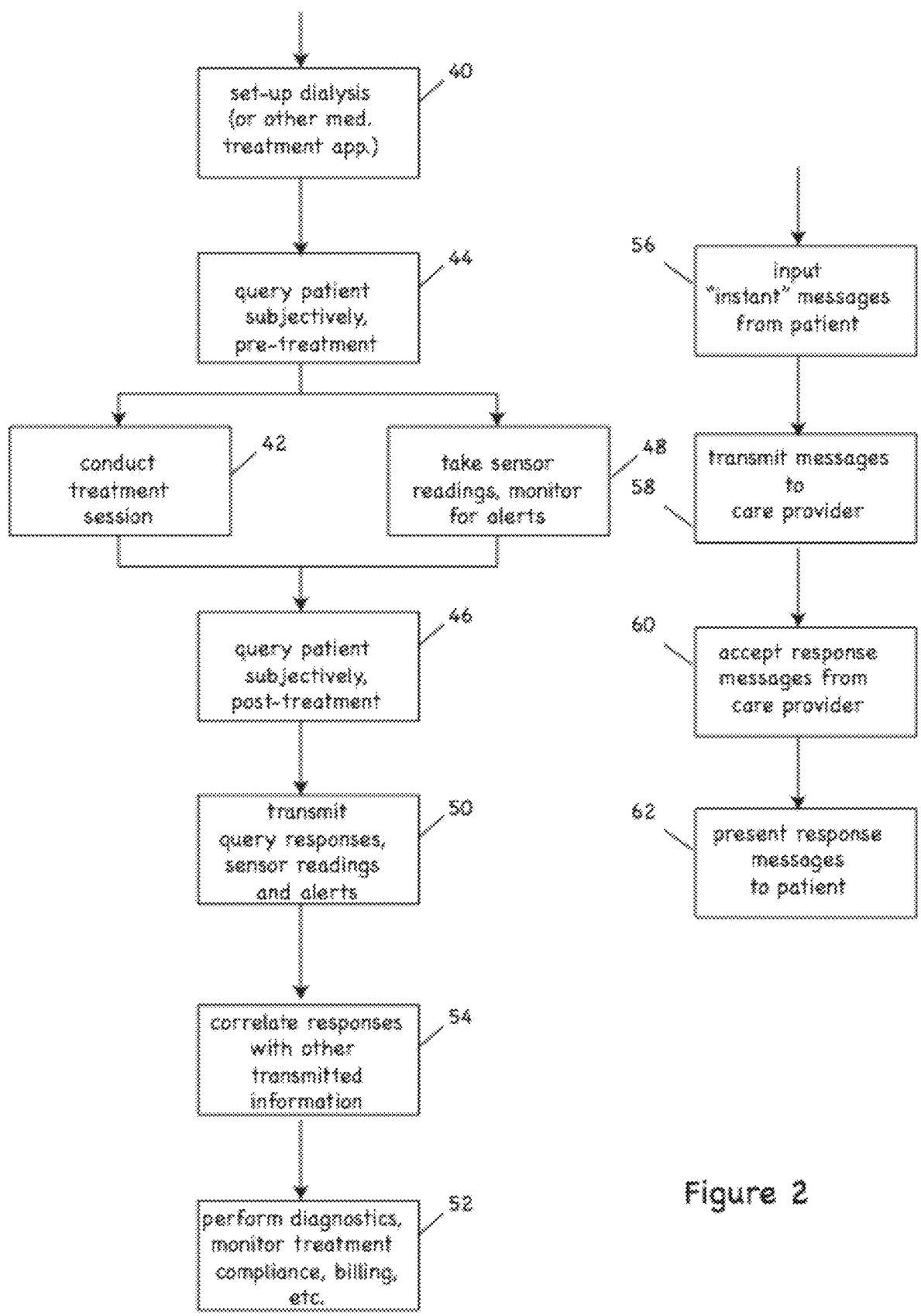
FIG. 2 depicts a method for operating a health care delivery device and system of FIG. 1.

FIG. 2 depicts operation of the system of FIG. 1 according to one practice of the invention. In step 40, apparatus 12 and sensors 28 are coupled to patient 20 and otherwise set-up for treatment delivery in the conventional manner known in the art (as adapted in accord with the teachings hereof).

In step 42, treatment is administered in the conventional manner known in the art, as adapted in accord with the teachings hereof. In connection with at least selected treatment sessions (e.g., every session, every other session, one session per week, or so forth), processor 14 generates queries to the patient 20. The queries can directed to, by way of non-limiting example, subjective topics, such as the patient's perception of his or her own mental health and well being, quality of life, degrees of pain, views on success of therapy, and so forth. The queries may include questions with yes/no answers, questions with a numeric grading, questions with a numeric value, and/or open-ended questions, etc. By way of example, queries designed to uncover depression (which has a correlation with patient morbidity and mortality) may include general questions regarding the emotional status of the patient and the quality of life and screens for depression. These may be questions to which the patient 20 responds with ratings, e.g., with values from one to five. The queries are not limited to subject topics and may include, for example, questions about the patient's eating habits, whether he/she is taking prescribed treatment medications and, if so, when and in what doses, and so forth.

In some embodiments, the processor generates specific queries based on the patient's underlying medical condition, medications and/or diagnoses (as reflected, for example, in start-up parameters for device 10 set at the time of installation or otherwise, e.g., by the health care provider). For example, based on such parameters, the processor can generate queries for a diabetic patient 20 regarding they took their prescribed insulin or whether they measured their fasting blood sugar, etc. In cases where treatment is rendered with assistance of a domestic or other care-giving partner, the queries can be directed to that person's perceptions of the patient's mental health and well being, etc., instead of or in addition to the patient's own perceptions.

The queries can be presented to the patient before, during and/or after the selected treatment session(s). See steps 44, 46. Preferably, in the case of pre- or post-treatment queries, they are generated sufficiently close in time (e.g., within an hour of treatment and, more preferably, within ½ hour of treatment and, still, more preferably within 10 minutes of treatment) to assure that the answers reflect the patient's state at the time of the treatment session.

In some embodiments, however, the processor 14 does not generate the queries in connection with selected treatment sessions per se. Rather, it generates the queries at a predetermined time, at a time selected ad hoc by the patient, or otherwise, on a daily, bi-daily, weekly, biweekly basis, or otherwise, regardless of treatment time. In such embodiments, the queries can nonetheless be directed to the patient's state in connection with the most recent treatment session(s) or otherwise.

Queries generated by the processor 14 are presented to the patient (and/or, for example, his/her domestic or other care-giving partner) via a liquid crystal display (LCD) 16 or other output device. Responses are input via keyboard or other input device 18. In the discussion that follows, the terms "patient query," "queries presented to patient," and the like, refer to the foregoing queries—regardless of whether they are presented to the patient directly or to his/her domestic or other care-giving partner. Likewise, the terms "response to query," "query responses," and the like, refer to responses to such queries—regardless of whether they are input by the patient directly or by his/her domestic or other care-giving partner.

In connection with at least selected treatment sessions—and, preferably, in connection with each treatment session—processor 14 acquires physiometric readings from sensors 28, operational readings from sensors 30, alerts (including incidence and duration information) from monitoring logic 32, and so forth. See step 48.

The communications logic (e.g., network interface 20) operates under control of the processor 14 to transmit query responses to the digital data processing system 24, along with readings from sensors 28, 30 and alerts from monitoring logic 32, for consideration by health care provider 22. See step 50. In the illustrated embodiment, those responses are transmitted e.g., at or around the time of completion of each treatment session, though, they can be transmitted at regular intervals (e.g., daily, weekly and so forth), e.g., when the device 10, network 26 and/or data processing system 24 is otherwise amenable to such transfer.

Alternatively, or in addition, the processor can store the query responses for each treatment session, along with readings from sensors 28, 30 and alerts from monitoring logic 32, to storage device 34, e.g., retaining the responses while awaiting transfer to the care provider. Indeed, in the case of such devices with removable media, the patient 20 can bring that with him/her to monthly evaluation sessions at the hospital, dialysis clinic or other center, for uploading to digital data processing system 24 and consideration by health care provider 22.

Health care provider 22 utilizes the information transferred from device 10 for on-going diagnosis and treatment of the patient (both on acute and chronic bases), as well as for decision support, monitoring treatment compliance, facilitating regulatory compliance, billing, and so forth. See step 52. Thus, for example, the health care provider can initiate printing or other reporting of some or all of the transferred information for the patient's medical record or flow sheet, for patient billing, and so forth. Alternatively, or in addition, such printing and/or reporting can be initiated by analysis/reporting module 24A. Likewise, the health care provider and/or module 24A can print or otherwise report all or selected portions of the transferred information to support reimbursement requests and/or refilling of prescriptions for medications (such as EPO) provided to the patient as part of the treatment regimen. This can include, for example, reporting drugs taken by the patient in connection with treatment, including, for example, when those drugs were taken and in what amounts. The foregoing will, among other things, ensure that the provider has sufficient documentation to prove use, for example, of EPO and other renal-related pharmaceuticals (Vitamin D analogues, iron preparations etc) in connection with treatment of the patient 20. The printing/reporting of this will also allow for notification or even adjustment of billing for these drugs.

To that end, analysis/reporting module 24A can analyze the information transmitted by device 10, including, correlating response queries, sensor readings and alerts transmitted by device 10 and/or data in the patient's 20 electronic medical record and database with (i) each other, (ii) prior responses, readings, conditions, alerts from the device and/or other information for the patient (e.g., from medical records), (iii) expected responses, readings, conditions and/or alerts, e.g., based on empirical, normative or other standards, and/or (iv) so forth, in order to facilitate the health care provider's understanding of individual or multiple treatment sessions (e.g., over week-, month-, three month-periods, and so forth) and, more generally, in on-going patient diagnosis and treatment (both on acute and chronic bases), decision support, monitoring treatment compliance, facilitating regulatory compliance, billing, and so forth. See step 54.

By way of non-limiting example, the module 24A can correlate response queries, sensor readings and alerts transmitted by device 10 with one another to identify discrepancies, e.g., between response queries and physiometric sensor readings (e.g., patient reports "feeling fine," yet sensors suggest high fever), between operational and/or physiometric sensor readings (e.g., operational readings show numerous treatment sessions, yet, physiometric readings suggest decline in patient condition), and so forth. The module 24A can also correlate response queries, sensor readings and alerts transmitted by device 10 with historical such data transmitted by that device for the same patient, e.g., to discern whether the patient is improving or falling out of compliance with a treatment regime. The module 24A can also correlate response queries, sensor readings and alerts transmitted by device 10 with empirical or normative standards, e.g., established for patients of similar demographics, by health care provider, treatment center, by the insurer, by government agencies, and so forth. Module 24A can, additionally, analyze the transmitted data to identify additional alarm conditions or data patterns (e.g., based on ad hoc or other input from the physician, nurse or other health care provider).

In addition to performing the foregoing analyses, module 24A can identify trends occurring over time in the results of those analyses and/or in the underlying data received from device 10, facilitating not only identification of chronic or long-term conditions. For example, the module can identify trends in the patient's responses to questions directed to general emotional status and can correlate those trends with objective or other data (e.g., from the patient's electronic medical record) and/or perform trend analysis that, for example, provides an early indication of burn-out and allow for a timely intervention.

Moreover, the module 24A can identify patterns and frequencies of alarms, alerts, treatment information, patient symptoms and/or responses which represent deviations from the patient, health care provider and/or treatment facility norms and indicate potential problems or inefficiencies for evaluation and correction. The number, frequency and pattern of machine alarms, alerts, the time required to clear an alarm and vital sign information (blood pressure and pulse measurements) can provide significant information about individual patients clinical condition and/or changes in their medical condition. It also provides information about care delivery issues during both home hemodialysis, peritoneal dialysis and/or in-center hemodialysis. In this latter regard, for the example, the module 24A can provide the foregoing correlations not only for a given patient, but also for a treatment facility, e.g., comparing statistics for query responses, sensor readings, and/or alerts for multiple patients of a given facility with those of other facilities and/or standards. The module 24A can generate reports or other documentation with the outcome(s) of those comparisons, e.g., in support of billing, regulatory compliance, and so forth. Thus, paralleling an advantage discussed above, the module 24A helps ensure that treatment facilities are doing as expected.

Illustrated analysis/reporting module 24A can report the information transmitted by device 10 and/or results of the foregoing analyses for use by the health care provider in providing on-going patient diagnosis and treatment (both on acute and chronic bases), decision support, monitoring treatment compliance, facilitating regulatory compliance, billing, and so forth. Moreover, module 24A can trigger an immediate alert (e.g., in the form of e-mail, text message or otherwise) to a physician, nurse or other health care provider and/or generate a printout/report allowing an assessment of the patient's prescription and/or other medical co-morbidities and diagnoses. For sake of simplicity, as used herein, the term "report" additionally encompasses notification of immediate alerts, unless otherwise evident from context.

In some embodiments, the processor 14 is adapted to perform some or all of the analyzes and reporting functions described above in connection with module 24A. The results of those analyses can be transmitted to digital data processor 24 and/or can form the basis of immediate reporting alerts, e.g., to the patient and/or the physician, nurse or other health care provider. Thus, for example, such alerts can be generated if user starts to performs unusual steps during in setup or treatment, e.g., failing to perform disinfection, performing operations out of order, attempting to improperly increase ultrafiltration setting, offering bizarre subjective responses indicating illness, distress and/or incoherence. In some embodiment, when the processor 14 detects such conditions, it stops or prevents further treatment, e.g., in addition to signaling an alert.

Figure 3A:
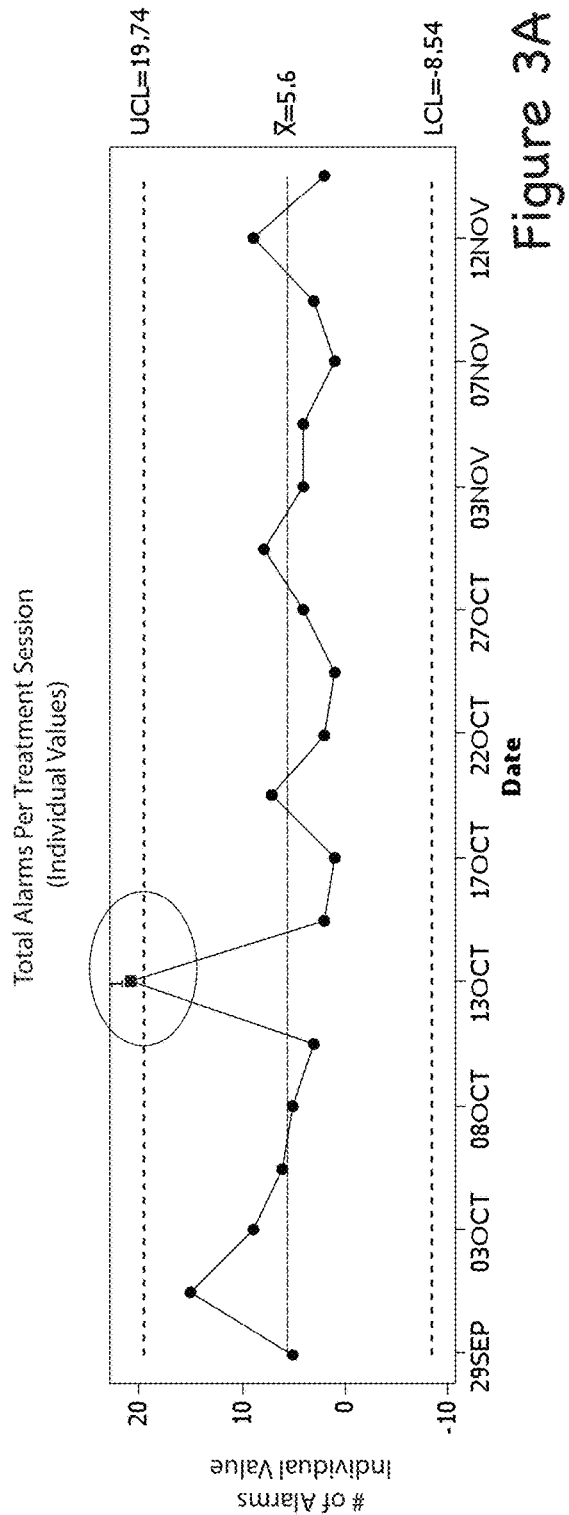
Figure 3B:
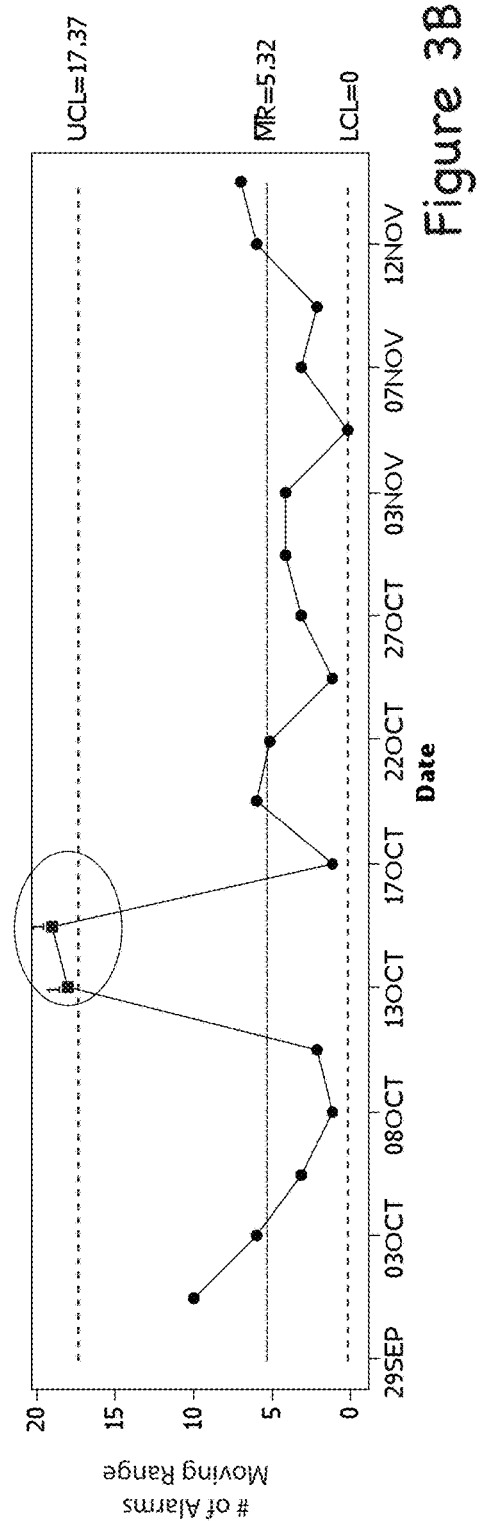

FIGS. 3A-3B depict examples of reports of the type generated by module 24A (and/or processor 14 providing like functionality) correlating alarm (or other) information transmitted from device 10 with clinical information. More particularly, FIG. 3A depicts an example of a chart of the type generated by module 24A plotting the total number of alarms per treatment session vs date for a given patient over multiple treatment sessions, here, illustrated as running between September 29 and November 12. The circled regions of the plots identify total alarm counts of interest, e.g., values running above an upper control limit ("UCL") or below a lower control limit ("LCL"), as well as other alarm counts of interest, e.g., as determined in accord with standard statistical control principles (or otherwise). Those counts may results from mistakes in the procedure executed by the patients, abnormal physiological conditions resulting from patient illness, erroneous operation of device 10 or otherwise.

Although the illustrated plot is for total alarm counts, the module 24A (and/or processor 14 providing like functionality) can provide like charts for specific alarms, groups of alarms and/or other values contained within the information transmitted from device 10. Moreover, although the illustrated plot is for an individual patient, the module 24A (and/or processor 14 providing like functionality) can provide like charts per treatment facility, per health care provider, or otherwise. Likewise, although the date axis in the drawing is by date, the module 24A (and/or processor 14 providing like functionality) can provide like charts by week, bi-week, month, quarter, and so forth.

FIG. 3B likewise depicts an example chart of the type generated by module 24A similar to that shown in FIG. 3A, though, plotting a moving range. As above, the circles regions indicate values of interest. And, although the illustrated plot is for a moving range of total alarm counts, the module 24A (and/or processor 14 providing like functionality) can provide like charts for moving ranges of specific alarm counts, of groups of alarms and/or of other values contained within the information transmitted from device 10. Moreover, although the illustrated plot is for an individual patient, the module 24A (and/or processor 14 providing like functionality) can provide like charts per treatment facility, per health care provider, or otherwise. Likewise, although the date axis in the drawing is by date, the module 24A (and/or processor 14 providing like functionality) can provide like charts by week, bi-week, month, quarter, and so forth.

With reference to FIGS. 3A-3B, module 24A can generate circles or indications of the sort shown to identify values of interest in the illustrated plots, or can rely on the physician, nurse or other health care provider, himself or herself, to discern the problematic readings. Where the module 24A generates those circles or other indications, they can be based on standard statistical control principles or otherwise.

Figure 4:
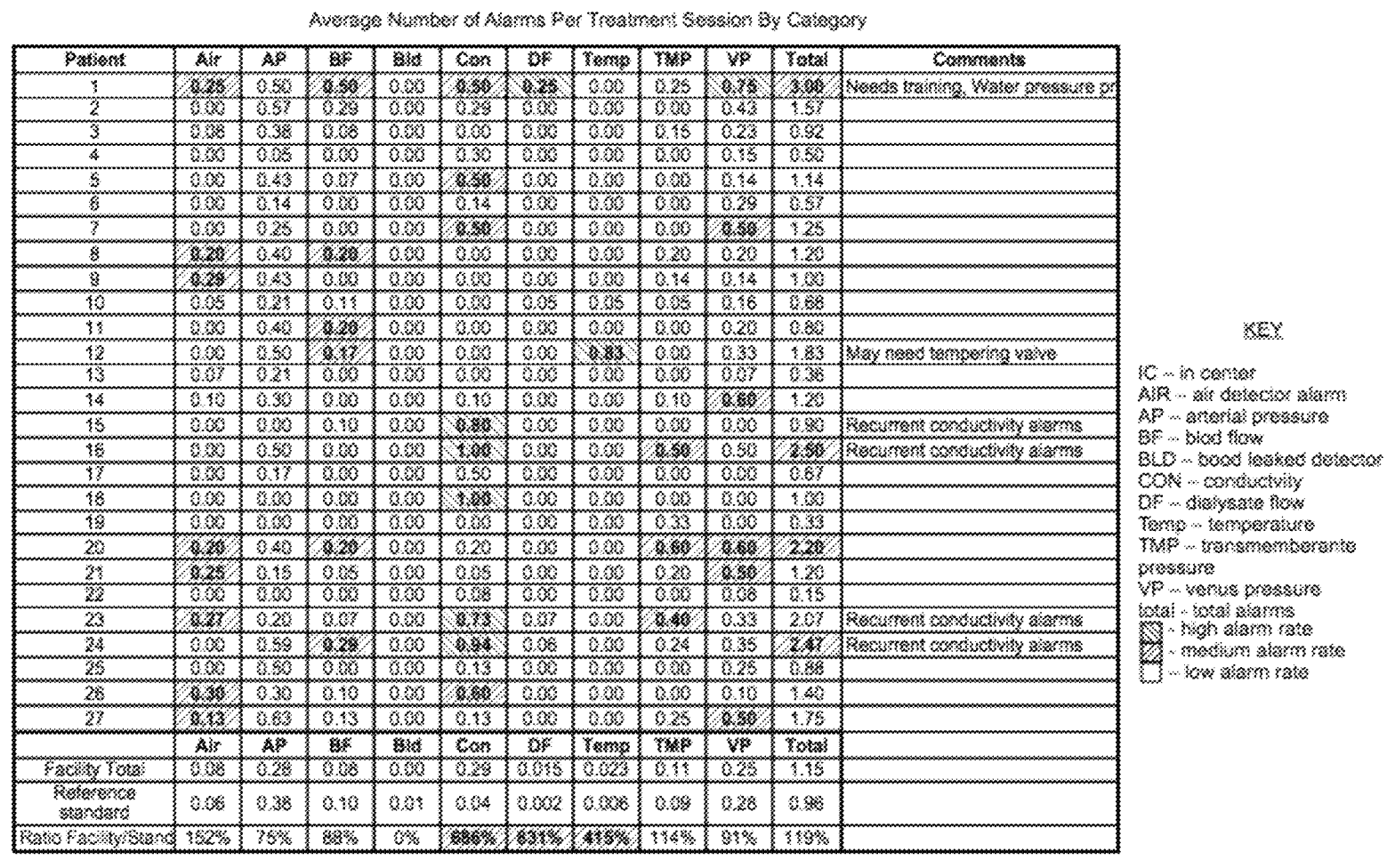

Module 24A can also generate patient and facility reports, as well as tabular "report cards" of the type shown in FIG. 4, by way of non-limiting example. That report lists, by patient, minimums, maximums, averages or other representative indications of the alarms, sensor readings or other data received from device 10 (here, indicated by abbreviations "Air", "AP", "BF", and so forth, along the top row of the chart). Also included on the illustrated report are comments by the health care provider, although, patient query responses, text messages (of the type described below) can be provided instead or in addition. The report can also provide totals for the identified patients, standards-based values, and comparisons therebetween, all as shown, by way of example, in the final three rows of the illustrated report.

The illustrated report includes colorations to identify readings or other values requiring physician, nurse or other health care provider attention. As above, module 24A can provide such coloration or indications on the generated reports, or can rely on the physician, nurse or other health care provider, himself or herself, to discern the problematic readings.

Analysis/reporting module 24A may generate the reports depicted in FIGS. 3-4 for printing or display, e.g., on LCD or other output device 24B. As well, these may be displayed on the liquid crystal display (LCD) or other output device 16 of device 10 in instances where it is deployed for access by the physician, nurse or other health care provider (e.g., when the device 10 is deployed at a hospital, dialysis clinic or other site).

Advantages of the analysis and reporting of query responses, sensor readings and alerts transmitted by device 10 and/or data in the patient's 20 electronic medical record as described herein and shown, by way of example, in FIGS. 3-4 are that it readily permits the physician, nurse or other health care provider to identify patients requiring medical attention, further training, counseling or other support. By way of further example, by reporting total number of alarms and time required to clear them, module 24A can be used to determine whether proper and efficient care is being delivered to the patient 20, and so forth.

This is advantageous over current practice, wherein clinicians respond to individual alarms and alerts but are not presented with patterns for individual treatments and for multiple treatment sessions that provide clinical context or normative references. This has heretofore prevented utilization of HHD-provided data to identify individual patient problems or issues with facility function or care delivery. This system will correct this gap and allow the full use of this additional and important information for care delivery and patient and facility oversight.

Messaging

In addition to the features discussed above, the aforementioned communications logic of device 10 can transmit text or other messages input by the patient via keyboard or other input device 18 to the health care provider. See steps 56, 58. The messages can be, for example, questions by the patient regarding his or her immediate or long-term treatment. They may be so-called "instant" messages that are transmitted in real-time (e.g., as the patient is entering them) to the digital data processing system 24 for presentation to care provider 22 and/or they can be queued for later transfer by the communications logic, e.g., along with the transfer query responses, sensor readings and alerts for each session. Though typically entered by the patient at the end of a treatment session, the keyboard or other input device 18 can accept a message from the patient (and the communications logic can transmit it) at any time the device 10 is operational.

The communications logic can, likewise, accept messages transmitted from the health care provider 22 via digital data processor 24. See step 60. Those messages, which may be, for example, responses to the patient's questions, suggestions on treatment, words of encouragement, and so forth, can be routed to processor 14 to LCD or other output device 16 for presentation to the patient. See step 62.

Although the communications logic can transmit text and other messages of the type just described between device 10 and digital data processor 24 via the same network 26 as is used for transfer of query responses, sensor readings and alerts for the treatment sessions, that communications logic can use other network media instead or in addition. Thus, for example, the communications logic can utilize the cellular phone network to transmit such messages (e.g., in the form of SMS messages or otherwise), while using an IP network such as the Internet to transfer the query responses, sensor readings and alerts for the treatment sessions. By way of further example, the communications logic can transmit such messages to a central monitoring system at digital processor 24, which then forwards them, e.g., via regular email, to a care delivery coordinator.

Systems for Health Care Delivery

Figure 5:
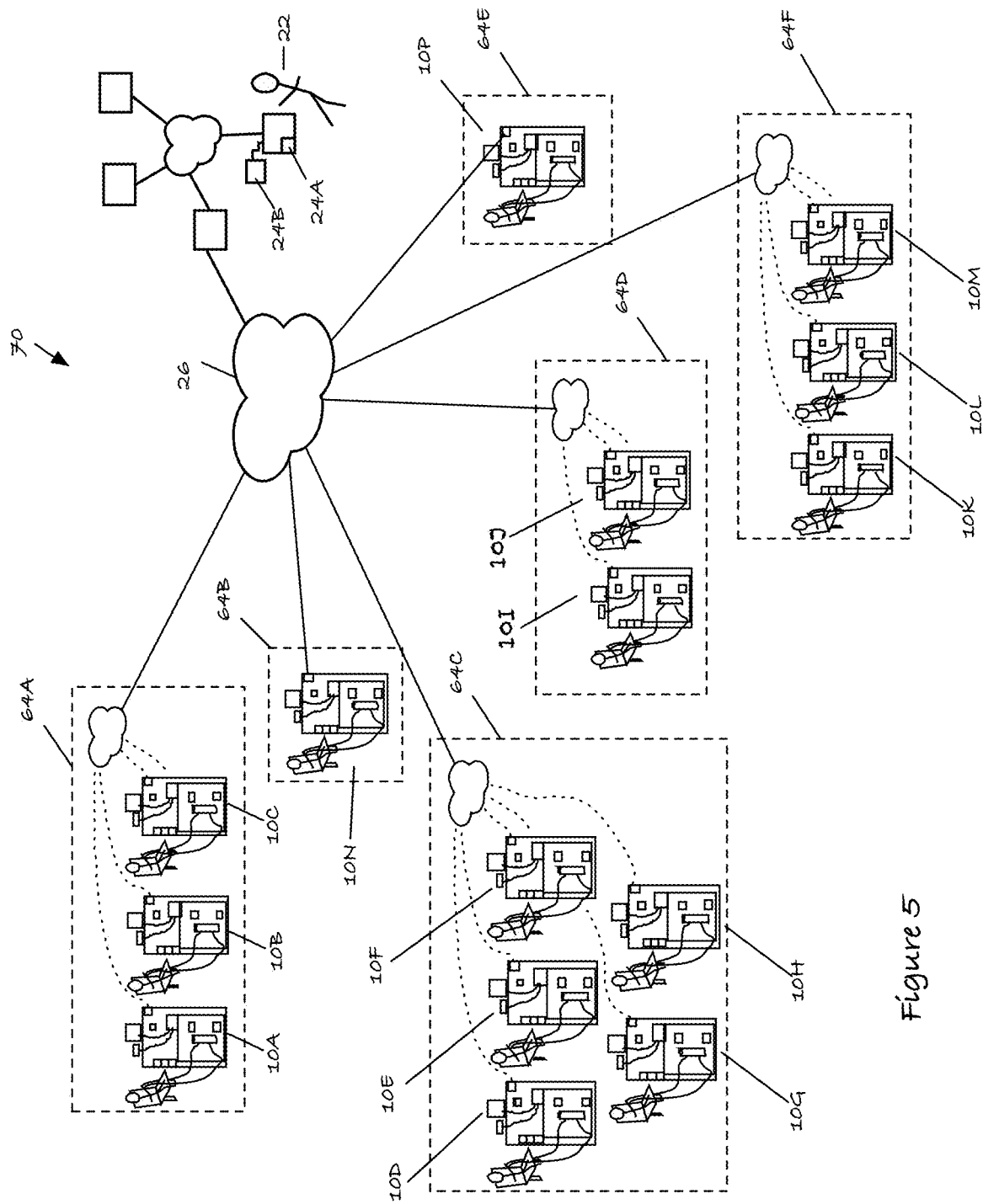
FIG. 5 depicts a system for health care delivery comprising a plurality of health care delivery devices of the type shown in FIG. 1.

FIG. 5 depicts a system for health care delivery comprising a plurality of health care delivery devices 10 of the type shown in FIG. 1 and discussed above, here, accordingly labeled 10A-10P. The devices 10A-10P are coupled via network media 26 to digital data processing system 24, as above, that includes analysis/reporting module 24A that (i) analyzes and/or reports the information collected from devices 10A-10P as discussed above and, further, below, and/or (ii) that optionally controls devices 10A-10P as discussed below.

Illustrated devices 10A-10P, which may comprise inter alia peritoneal dialysis or other medical treatment apparatus, are constructed and operated as described above as further adapted in accord with the teachings that follow. As indicated by dashed-line boxes, devices 10A-10P are disposed in "treatment centers" 64A-64F that range in size from stand-alone instances in patient homes to multiples of such devices in commercial facilities such as hospitals, dialysis centers or other central locations (and/or departments, floors, wards and/or rooms of such facilities), all by way of non-limiting example.

As discussed above, system 24 and, specifically, for example, module 24A analyzes sensor readings, alerts and other information provided by the devices 10A-10P, e.g., to identify and report deviations from norms of patient care. Examples of this are shown in FIGS. 3A-3B and are discussed above.

FIG. 6 provide a further example, to wit, a chart-style report of the type generated by module 24A showing comparative treatment data for multiple commercial health care facilities (e.g., dialysis centers) and, more particularly, showing for each of eight treatment centers 64A-64F over a designated time period (e.g., one month) a number of patients treated, a total number of treatments, a percentage of treatments in which the patient was hypotensive, an average number of alarms per treatment, an average number of alarm-minutes per treatment, and the average number of alarm-minutes per alarm. The figures presented by module 24A in the chart of FIG. 6 are a result of an analysis by module 24A of raw data extracted from information uploaded by the devices 10A-10P to the digital data processor 24, particularly, in this example, an arithmetic and statistical analysis. Other reports may be prepared utilizing the raw data itself and/or results of other analyses.

With continued reference to FIG. 6, in addition to presenting data (raw, analyzed of otherwise) from the devices 10A-10P in a report and/or alert, module 24A (i) identifies in that data (and/or in underlying information from the devices 10A-10P) deviations that potentially reflect differences in care offered by the treatment centers 64A-64F, and (ii) formats or other modifies the report to reflect those deviations. The module 24A may uncover those deviations, as noted above, in numbers, frequencies and patterns of machine alarms, alerts, times required to clear alarm, vital sign information, and so forth, by way of example. In the illustrated example that is FIG. 6, module 24A generates the report of FIG. 6 highlighting the hypotension, alarms per treatment and alarm-minutes per treatment entries for treatment center #5, along with the alarm minutes per alarm entry for treatment center #6, indicating that the devices, personnel and/or procedures used in those centers did not operate to par with the other centers (at least in regards reflected by the respective highlighted statistics) during the period covered by the chart.

While in some embodiments, the module 24A can identify (and report on) discrepancies in the raw and/or analyzed data from the devices 10A-10P, module 24A of other embodiments can, in addition, infer and report on possible causes of those discrepancies, thereby, providing automated operations support for the treatment centers.

More generally, the module 24A can identify patterns in data received from multiple devices 10A-10P (e.g., in a given treatment center, in a given region geographic region, etc.) and can infer therefrom and/or from like data received from other such devices (e.g., at other treatment centers, other geographic regions, etc.) causes of discrepancies reflected in those patterns, e.g., resulting from (i) the operation of individual such devices or groups of such devices (e.g., at the given treatment center), (ii) care offered to patients treated by those devices, and/or (iii) patient demographics, among other factors. This may be based on, for example, heart rate, blood pressure, temperature, oxygen (O20 saturation, blood volume, blood flow, dialysate flow, conductivity, dialyzer clearance, alarm state, venous pressure, arterial pressure, and/or other information regarding the patients and/or the health care delivery devices, as provided by the aforementioned sensors or otherwise.

In addition, the module 24A of some embodiments can, instead or in addition, effect changes in operation of the devices 10A-10P to facilitate correction of those causes, e.g., the setting off or resetting of alarms, recalibration of sensors, blocking or unblocking device operation, communicating or implementing a physician-ordered prescription, and so forth—all by way of example. Such changes can be effected indirectly, e.g., through alerting of (and action by) a technician or other personnel (e.g., physician, nurse or other health care provider) local to the device being controlled, or directly, e.g., through transmission of control signals to suitably equipped such devices 10A-10P (e.g., a device equipped for remote control) via network 26 and the aforesaid communications logic.

Figure 7:
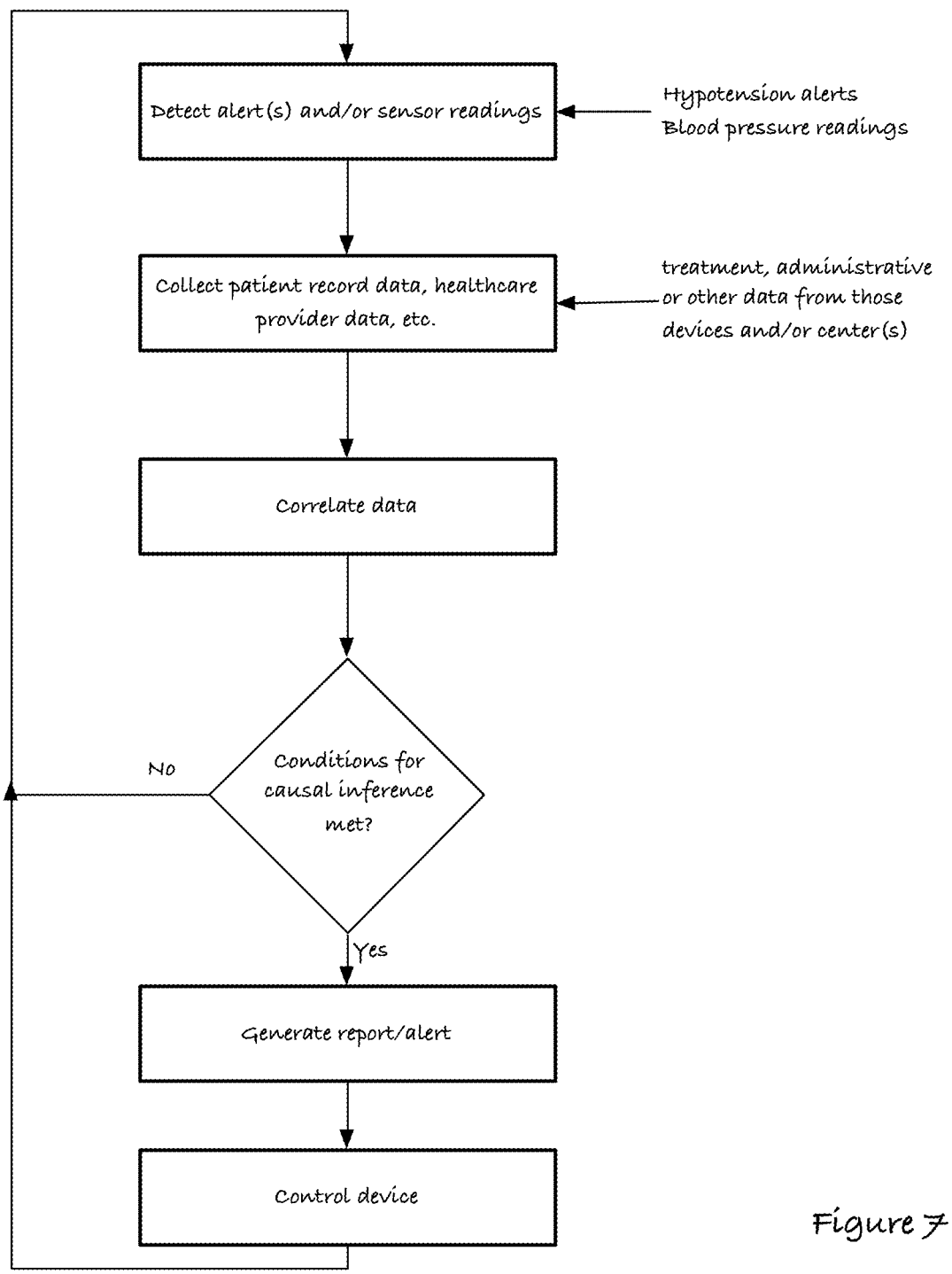
FIG. 7 depicts a method for such inferential reporting on and/or control of patient in a system according to the invention.

A flow chart depicting operation of embodiments that provide for such inferential reporting on and/or control of treatment is provided in FIG. 7, examples of which are described in the text that follows.

Dry Weight Adjustment

Thus, for example, in embodiments where devices 10A-10P comprise dialysis units and, more particularly, for example, hemodialysis units, module 24A can (i) infer from patterns of hypotension reflected in data from the devices 10A-10P (raw, analyzed of otherwise) that patients under care by those devices at one or more treatment centers 64A-64F may require "dry weight" adjustment, and (ii) generate reports and/or immediate alerts directing health care providers and/or others at affected treatment centers of a possible need to make such adjustment.

Instead of, or in addition to generating such reports and/or alerts, module 24A of some embodiments can control the devices 10A-10P to facilitate adjustment of dry weight on a per-patient, per-provider or other basis. In addition, that module 24A can effect changes in operation of the devices 10A-10P, e.g., the setting or resetting of alarms, recalibration of sensors, blocking or unblocking of device operation, communicating or implementing a physician-ordered prescription, and so forth—all by way of example. Such changes can be effected indirectly, e.g., through alerting of (and action by) a technician or other personnel (e.g., physician, nurse or other health care provider) local to the device being controlled, or directly, e.g., through signaling of a suitably equipped such device 10A-10P (e.g., a device equipped for remote control) via network 26 and the aforesaid communications logic.

Dry weight, as used here, is a treatment parameter representing, e.g., what each patient would weigh in the absence of kidney disease and, therefore, determining how much fluid should be removed from the patient during a treatment session by devices 10A-10P. Likewise, hypotension refers to a condition in which a patient's systolic blood pressure (SBP) is less than 90 mmHg and decreases more than 30 mmHg from maximum SBP during a treatment session by devices 10A-10P. In other embodiments, dry weight and hypotension may be defined otherwise consistent with the teachings hereof.

Particularly, for example, module 24A can infer from hypotension alerts signaled (and/or blood pressure readings taken) by a device, e.g., device 10K, during treatment of a single patent in a single treatment session that the patient may require dry weight adjustment, and can generate reports and/or immediate alerts as discussed above in order to alert that health care providers and/or others associated with that treatment center 64F. In the illustrated embodiment, the module 24A makes such an inference whenever the sensors of the treating device, here, 10K, detect even a single instance of hypotension (as defined above) during a treatment session. In other embodiments, this can be conditioned on detection of multiple (e.g., three or more) such instances during a session. In yet other embodiments, it can be conditioned on detection of such condition or conditions over multiple treatment sessions of the same patient (e.g., detection of two or more incidents in at least three out of five consecutive treatment sessions for that patient).

In addition to, or instead of, reporting on the possible need for dry weight adjustment, module 24A of some embodiments can, instead or in addition, effect changes in operation of the devices 10A-10P to facilitate such adjustment, e.g., through signaling of a suitably equipped such device 10K to correct any dry weight values input to the device (e.g., by the health care provider) in connection with treatment of the patient.

Instead or in addition, module 24A of the embodiment of FIG. 5 can infer, by cross-correlating hypotension alerts signaled (and/or blood pressure readings taken) by one or more devices of a single center (e.g., devices 10K-10M of center 64F) or of multiple centers (e.g., devices 10I-10J, 10K-10M, 10P of centers 64D-64F) with treatment, administrative or other data from those devices and/or center(s), that patients under the care of a specific device or devices, specific health care provider (e.g., dialysis nurse and/or physician) or group of providers (e.g., personnel of a given center, personnel trained by a specific trainer, and so forth) may require dry weight adjustment. In the illustrated embodiment, the module 24A makes such an inference whenever the cross-correlations suggest that hypotension-producing treatments associated with a given such device or provider (or group thereof) deviate statistically significantly from health care provider, treatment facility or other norms. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for dry weight adjustment, module 24A of some embodiments can, instead or in addition, effect changes in operation of the devices (e.g., 10I-10J, 10K-10M, 10P) to facilitate such adjustment, e.g., through signaling of those devices to correct any dry weight values input to in connection with treatment of patients under the care of a specific health care provider (e.g., dialysis nurse and/or physician) or group of providers While module 24A can infer that a given (group of) patient(s) may require dry weight adjustment as discussed above, in some embodiments, module 24A can infer from similar data that sensors of one or more devices 10A-10P may be signaling false hypotension alerts and/or providing incorrect blood pressure readings. To this end, module 24A can generate reports and/or immediate alerts in order to alert the health care providers and/or others of the possible need for device maintenance by drawing such an inference from cross-correlation of hypotension alerts signaled (and/or blood pressure readings taken) by multiple devices of a single center (e.g., devices 10K-10M of center 64F) or of multiple centers (e.g., devices 10I-10J, 10K-10M, 10P of centers 64D-64F) with treatment, administrative or other data from those devices and/or center(s) suggesting that a pattern or frequency of hypotension-producing alarms (or sensor readings) associated with a single such device deviates statistically significantly from those of other devices, e.g., when factors such as patient treated, health care provider delivering treatment, etc. are factored out. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for device maintenance of a device or devices per the above, module 24A of some embodiments can, instead or in addition, effect changes in operation of the devices requiring such maintenance, e.g., through signaling of those devices to recalibrate blood pressure sensors, reset hypotension alarms, and so forth, by way of example.

Medication Adjustment

By way of further example, in embodiments where devices 10A-10P comprise dialysis units and, more particularly, for example, hemodialysis units, module 24A can (i) infer from patterns of hypotension reflected in data from the devices 10A-10P (raw, analyzed of otherwise), as well, optionally, as from supplemental infusate supplies, sensors and/or monitoring logic of those devices 10A-10P that detect medication supplies and/or dosings, that patients under care by those devices at one or more treatment centers 64A-64F may require medication adjustment, and (ii) generate reports and/or immediate alerts directing health care providers and/or others at affected treatment centers of a possible need to make such adjustments and/or control the devices 10A-10P to facilitate such adjustment on a per-patient, per-provider or other basis.

Particularly, for example, module 24A can infer from hypotension alerts signaled (and/or blood pressure readings taken) by a device, e.g., device 10K, as well, optionally, as from alerts and/or readings from a supplemental infusate supply, sensor and/or monitoring logic of that device, during treatment of a single patent in a single treatment session that the patient may require medication adjustment, and can generate reports and/or immediate alerts as discussed above in order to alert health care providers and/or others associated with that treatment center 64F. In the illustrated embodiment, the module 24A makes such an inference whenever the sensors of the treating device, here, 10K, detect a single instance of hypotension (as defined above) during a treatment session. In other embodiments, this can be conditioned on detection of multiple such instances during a session, e.g., coupled with alerts and/or sensor readings indicating that dosings of medication by device 10K are below a threshold value (e.g., a maximum dose, a dosage in the 75th quartile, etc.). In yet other embodiments, it can be conditioned on detection of such condition or conditions over multiple treatment sessions of the same patient (e.g., detection of two or more hypotension incidents coupled with sub-threshold dosings in at least three out of five consecutive treatment sessions for that patient).

In addition to, or instead of, reporting on the possible need for medication adjustment, module 24A of some embodiments can, instead or in addition, effect changes in operation of the devices 10K to facilitate such adjustment, e.g., through signaling of a suitably equipped such device 10K to modify dosages in connection with treatment of the patient. Typically, such control is effected along with an alert to processor 14 and accompanying display on LCD 16 of device 10K necessitating confirmation of the change by a health care provider via keyboard 18 before it makes further treatment of the patient.

Instead or in addition, module 24A of the embodiment of FIG. 5 can infer, by cross-correlating hypotension alerts signaled (and/or blood pressure readings taken) by one or more devices of a single center (e.g., devices 10K-10M of center 64F) or of multiple centers (e.g., devices 10I-10J, 10K-10M, 10P of centers 64D-64F) as well, optionally, from alerts and/or readings from a supplemental infusate supplies, sensors and/or monitoring logic of those devices, with treatment, administrative or other data from those devices and/or center(s), that patients under the care of a specific device or devices or a specific health care provider (e.g., dialysis nurse and/or physician) or group of providers (e.g., personnel of a given center, personnel trained by a specific trainer, and so forth) may require medication adjustment. In the illustrated embodiment, the module 24A makes such an inference whenever the cross-correlations suggest that hypotension-producing treatments and medication dosings associated with a given such device or provider (or group thereof) deviate statistically significantly from health care provider, treatment facility or other norms. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for medication adjustment, module 24A of some embodiments can, instead or in addition, effect changes in operation of the devices (e.g., 10I-10J, 10K-10M, 10P) to facilitate such adjustment, e.g., through signaling of those devices to modify dosages in connection with treatment of patients under the care of a specific health care provider (e.g., dialysis nurse and/or physician) or group of providers. As above, typically such control is effected along with an alert to processors 14 and accompanying displays on LCDs 16 of the respective devices necessitating confirmation of the changes via keyboards 18 before they carry out further treatment of the patient.

While module 24A can infer that a given (group of) patient(s) may require medication adjustment as discussed above, in some embodiments, module 24A can infer from similar data that sensors of one or more devices 10A-10P may be signaling false hypotension or medication alerts, and/or providing incorrect blood pressure and/or medication dosage readings. To this end, module 24A can generate reports and/or immediate alerts in order to alert the health care providers and/or others of the possible need for device maintenance in these regards upon drawing such an inference when cross-correlation of hypotension alerts signaled (and/or blood pressure readings taken) by multiple devices of a single center (e.g., devices 10K-10M of center 64F) or of multiple centers (e.g., devices 10I-10J, 10K-10M, 10P of centers 64D-64F) as well, optionally, as from alerts and/or readings from a supplemental infusate supplies, sensors and/or monitoring logic of those devices, with treatment, administrative or other data from those devices and/or center(s) suggest that a pattern or frequency of hypotension-producing and/or medication dosing-related alarms (or sensor readings) associated with a single such device deviate statistically significantly from those of other devices, e.g., when factors such as patient treated, health care provider delivering treatment, etc. are factored out. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for device maintenance of a device or devices per the above, module 24A of some embodiments can, instead or in addition, effect changes in operation of the devices requiring such maintenance, e.g., through signaling of those devices to recalibrate sensors, reset alarms, and so forth, by way of example.

Filtration Rate Adjustment

By way of further example, in embodiments where devices 10A-10P comprise dialysis units and, more particularly, for example, hemodialysis units, module 24A can (i) infer from patterns of hypotension reflected in data from the devices 10A-10P (raw, analyzed of otherwise), as well, optionally, as from sensors and/or monitoring logic of those devices 10A-10P that detect filtration rates, that patients under care at one or more treatment centers 64A-64F may require filtration rate adjustment, and (ii) generate reports and/or immediate alerts directing health care providers and/or others at affected treatment centers of a possible need to make such adjustments and/or control the devices 10A-10P to facilitate such adjustment on a per-patient, per-provider or other basis.

Particularly, for example, module 24A can infer from hypotension alerts signaled (and/or blood pressure readings taken) by a device, e.g., device 10K, as well, optionally, as from filtration rate alerts and/or readings from sensors and/or monitoring logic of that device, during treatment of a single patent in a single treatment session that the patient may require filtration rate adjustment, and can generate reports and/or immediate alerts as discussed above in order to alert that health care providers and/or others associated with that treatment center 64F. In the illustrated embodiment, the module 24A makes such an inference whenever the sensors of the treating device, here, 10K, detect a single instance of hypotension (as defined above) during a treatment session. In other embodiments, this can be conditioned on detection of multiple such instances during a session, e.g., coupled with alerts and/or sensor readings indicating that filtration rates by device 10K are below a threshold value. In yet other embodiments, it can be conditioned on detection of such condition or conditions over multiple treatment sessions of the same patient (e.g., detection of two or more hypotension incidents coupled with above-threshold filtration rates in at least three out of five consecutive treatment sessions for that patient).

In addition to, or instead of, reporting on the possible need for filtration rate adjustment, module 24A of some embodiments can, instead or in addition, effect changes in operation of the devices 10K to facilitate such adjustment, e.g., through signaling of a suitably equipped such device 10K to modify filtration rates in connection with treatment of the patient. Typically, such control is effected along with an alert to processor 14 and accompanying display on LCD 16 of device 10K necessitating confirmation of the change by a health care provider via keyboard 18 before it makes further treatment of the patient.

Instead or in addition, module 24A of the embodiment of FIG. 5 can infer, by cross-correlating hypotension alerts signaled (and/or blood pressure readings taken) by one or more devices of a single center (e.g., devices 10K-10M of center 64F) or of multiple centers (e.g., devices 10I-10J, 10K-10M, 10P of centers 64D-64F) as well, optionally, from filtration rate alerts and/or readings from sensors and/or monitoring logic of those devices, with treatment, administrative or other data from those devices and/or center(s), that patients under the care of a specific device or group of devices, a specific health care provider (e.g., dialysis nurse and/or physician) or group of providers (e.g., personnel of a given center, personnel trained by a specific trainer, and so forth) may require filtration rate adjustment. In the illustrated embodiment, the module 24A makes such an inference whenever the cross-correlations suggest that hypotension-producing treatments and filtration rates associated with a given such provider (or group) deviate statistically significantly from health care provider, treatment facility or other norms. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for filtration rate adjustment, module 24A of some embodiments can, instead or in addition, effect changes in operation of the devices (e.g., 10I-10J, 10K-10M, 10P) to facilitate such adjustment, e.g., through signaling of those devices to modify filtration rates in connection with treatment of patients under the care of a specific health care provider (e.g., dialysis nurse and/or physician) or group of providers. As above, typically such control is effected along with an alert to processors 14 and accompanying displays on LCDs 16 of the respective devices necessitating confirmation of the changes via keyboards 18 before they carry out further treatment of the patient.

While module 24A can infer that a given (group of) patient(s) may require filtration rate adjustment as discussed above, in some embodiments, module 24A can infer from similar data that sensors of one or more devices 10A-10P may be signaling false hypotension or filtration rate alerts, and/or providing incorrect blood pressure and/or filtration rate readings. To this end, module 24A can generate reports and/or immediate alerts in order to alert the health care providers and/or others of the possible need for device maintenance in these regards upon drawing such an inference when cross-correlation of hypotension alerts signaled (and/or blood pressure readings taken) by multiple devices of a single center (e.g., devices 10K-10M of center 64F) or of multiple centers (e.g., devices 10I-10J, 10K-10M, 10P of centers 64D-64F) as well, optionally, as from filtration rate alerts and/or readings from sensors and/or monitoring logic of those devices, with treatment, administrative or other data from those devices and/or center(s) suggest that a pattern or frequency of hypotension-producing and/or filtration-related alarms (or sensor readings) associated with a single such device deviate statistically significantly from those of other devices, e.g., when factors such as patient treated, health care provider delivering treatment, etc. are factored out. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for device maintenance of a device or devices per the above, module 24A of some embodiments can, instead or in addition, effect changes in operation of the devices requiring such maintenance, e.g., through signaling of those devices to recalibrate sensors, reset alarms, and so forth, by way of example.

Dialysate Temperature Adjustment

By way of further example, in embodiments where devices 10A-10P comprise dialysis units and, more particularly, for example, hemodialysis units, module 24A can (i) infer from patterns of hypotension reflected in data from the devices 10A-10P (raw, analyzed of otherwise), as well, optionally, as from sensors and/or monitoring logic of those devices 10A-10P that detect patient internal body temperatures and fresh/incoming dialysate temperatures, that patients under care at one or more treatment centers 64A-64F may require dialysate temperature adjustment, and (ii) generate reports and/or immediate alerts directing health care providers and/or others at affected treatment centers of a possible need to make such adjustments and/or control the devices 10A-10P to facilitate such adjustment on a per-patient, per-provider or other basis.

Particularly, for example, module 24A can infer from hypotension alerts signaled (and/or blood pressure readings taken) by a device, e.g., device 10K, as well, optionally, as from dialysate temperature alerts and/or readings from sensors and/or monitoring logic of that device that monitor temperatures of the patient and fresh/incoming dialysate, during treatment of a single patent in a single treatment session that the patient may require dialysate temperature adjustment, and can generate reports and/or immediate alerts as discussed above in order to alert that health care providers and/or others associated with that treatment center 64F. In the illustrated embodiment, the module 24A makes such an inference whenever the sensors of the treating device, here, 10K, detect a single instance of hypotension (as defined above) during a treatment session. In other embodiments, this can be conditioned on detection of multiple such instances during a session, e.g., coupled with alerts and/or sensor readings indicating that dialysate temperatures by device 10K are below a threshold value. In yet other embodiments, it can be conditioned on detection of such condition or conditions over multiple treatment sessions of the same patient (e.g., detection of two or more hypotension incidents coupled with above-threshold dialysate temperatures in at least three out of five consecutive treatment sessions for that patient).

In addition to, or instead of, reporting on the possible need for dialysate temperature adjustment, module 24A of some embodiments can, instead or in addition, effect changes in operation of the devices 10K to facilitate such adjustment, e.g., through signaling of a suitably equipped such device 10K to modify dialysate temperatures in connection with treatment of the patient. Typically, such control is effected along with an alert to processor 14 and accompanying display on LCD 16 of device 10K necessitating confirmation of the change by a health care provider via keyboard 18 before it makes further treatment of the patient.

Instead or in addition, module 24A of the embodiment of FIG. 5 can infer, by cross-correlating hypotension alerts signaled (and/or blood pressure readings taken) by one or more devices of a single center (e.g., devices 10K-10M of center 64F) or of multiple centers (e.g., devices 10I-10J, 10K-10M, 10P of centers 64D-64F) as well, optionally, from dialysate temperature alerts and/or readings from sensors and/or monitoring logic of those devices, with treatment, administrative or other data from those devices and/or center(s), that patients under the care of a specific device or group of devices, a specific health care provider (e.g., dialysis nurse and/or physician) or group of providers (e.g., personnel of a given center, personnel trained by a specific trainer, and so forth) may require dialysate temperature adjustment. In the illustrated embodiment, the module 24A makes such an inference whenever the cross-correlations suggest that hypotension-producing treatments and fresh/incoming dialysate temperatures associated with a given such provider (or group) deviate statistically significantly from health care provider, treatment facility or other norms. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for dialysate temperature adjustment, module 24A of some embodiments can, instead or in addition, effect changes in operation of the devices (e.g., 10I-10J, 10K-10M, 10P) to facilitate such adjustment, e.g., through signaling of those devices to modify dialysate temperatures in connection with treatment of patients under the care of a specific health care provider (e.g., dialysis nurse and/or physician) or group of providers. As above, typically such control is effected along with an alert to processors 14 and accompanying displays on LCDs 16 of the respective devices necessitating confirmation of the changes via keyboards 18 before they carry out further treatment of the patient.

While module 24A can infer that a given (group of) patient(s) may require dialysate temperature adjustment as discussed above, in some embodiments, module 24A can infer from similar data that sensors of one or more devices 10A-10P may be signaling false hypotension or dialysate temperature alerts, and/or providing incorrect blood pressure and/or dialysate temperature readings. To this end, module 24A can generate reports and/or immediate alerts in order to alert the health care providers and/or others of the possible need for device maintenance in these regards upon drawing such an inference when cross-correlation of hypotension alerts signaled (and/or blood pressure readings taken) by multiple devices of a single center (e.g., devices 10K-10M of center 64F) or of multiple centers (e.g., devices 10I-10J, 10K-10M, 10P of centers 64D-64F) as well, optionally, as from dialysate temperature alerts and/or readings from sensors and/or monitoring logic of those devices, with treatment, administrative or other data from those devices and/or center(s) suggest that a pattern or frequency of hypotension-producing and/or dialysate temperature-related alarms (or sensor readings) associated with a single such device deviate statistically significantly from those of other devices, e.g., when factors such as patient treated, health care provider delivering treatment, etc. are factored out. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for device maintenance of a device or devices per the above, module 24A of some embodiments can, instead or in addition, effect changes in operation of the devices requiring such maintenance, e.g., through signaling of those devices to recalibrate sensors, reset alarms, and so forth, by way of example.

Blood Clotting

By way of further example, in further embodiments, module 24A can (i) infer from patterns of atrial and venus pressure alerts reflected in data from the devices 10A-10P (raw, analyzed of otherwise) that patients under care at one or more treatment centers 64A-64F may require adjustment of anticoagulant medications and/or vascular access evaluation to prevent excessive clotting, and (ii) generate reports and/or immediate alerts directing health care providers and/or others at affected treatment centers of a possible need to make such adjustments and/or control the devices 10A-10P to facilitate such adjustment on a per-patient, per-provider or other basis.

Particularly, for example, module 24A can infer from venus and/or atrial pressure alerts signaled (and/or port blood flow readings taken) by a device, e.g., device 10K during treatment of a single patent in a single treatment session that the patient may require anticoagulant medication adjustment and/or vascular access evaluation, and can generate reports and/or immediate alerts as discussed above in order to alert that health care providers and/or others associated with that treatment center 64F. In the illustrated embodiment, the module 24A makes such an inference whenever the sensors of the treating device, here, 10K, detect a single venous or arterial pressure alert (or out of bounds sensor reading) during a treatment session. In other embodiments, this can be conditioned on detection of multiple such instances during a session. In yet other embodiments, it can be conditioned on detection of such condition or conditions over multiple treatment sessions of the same patient (e.g., detection of two or more venous or arterial pressure alert in at least three out of five consecutive treatment sessions for that patient).

In addition to, or instead of, reporting on the possible need for anticoagulant medication adjustment and/or vascular access evaluation, module 24A of some embodiments can, instead or in addition, effect changes in operation of the devices 10K to facilitate such adjustment, e.g., through signaling of a suitably equipped such device 10K to infuse such medication into the dialysate in connection with treatment of the patient. Typically, such control is effected along with an alert to processor 14 and accompanying display on LCD 16 of device 10K necessitating confirmation of the change by a health care provider via keyboard 18 before it makes further treatment of the patient.

Instead or in addition, module 24A of the embodiment of FIG. 5 can infer, by cross-correlating venous or arterial pressure alert signaled (and/or blood flow readings taken) by one or more devices of a single center (e.g., devices 10K-10M of center 64F) or of multiple centers (e.g., devices 10I-10J, 10K-10M, 10P of centers 64D-64F) with treatment, administrative or other data from those devices and/or center(s), that patients under the care of a specific device or group of devices and/or of a specific health care provider (e.g., dialysis nurse and/or physician) or group of providers (e.g., personnel of a given center, personnel trained by a specific trainer, and so forth) may require anticoagulant medication adjustment and/or vascular access evaluation. In the illustrated embodiment, the module 24A makes such an inference whenever the cross-correlations suggest that venous or arterial pressure alert-producing treatments associated with a given such provider (or group) deviate statistically significantly from health care provider, treatment facility or other norms. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for anticoagulant medication adjustment, module 24A of some embodiments can, instead or in addition, effect changes in operation of the devices (e.g., 10I-10J, 10K-10M, 10P) to facilitate such adjustment, e.g., through signaling of those devices to modify amounts of anticoagulant infused into dialysates in connection with treatment of patients under the care of a specific health care provider (e.g., dialysis nurse and/or physician) or group of providers. As above, typically such control is effected along with an alert to processors 14 and accompanying displays on LCDs 16 of the respective devices necessitating confirmation of the changes via keyboards 18 before they carry out further treatment of the patient.

While module 24A can infer that a given (group of) patient(s) may require anticoagulant medication adjustment and/or vascular access evaluation as discussed above, in some embodiments, module 24A can infer from similar data that sensors of one or more devices 10A-10P may be signaling false venous or arterial pressure alerts. To this end, module 24A can generate reports and/or immediate alerts in order to alert the health care providers and/or others of the possible need for device maintenance in these regards upon drawing such an inference when cross-correlation of venous or arterial pressure alert signaled (and/or blood flow readings taken) by multiple devices of a single center (e.g., devices 10K-10M of center 64F) or of multiple centers (e.g., devices 10I-10J, 10K-10M, 10P of centers 64D-64F) with treatment, administrative or other data from those devices and/or center(s) suggest that a pattern or frequency of venous or arterial pressure alerts (or blood flow sensor readings) associated with a single such device deviate statistically significantly from those of other devices, e.g., when factors such as patient treated, health care provider delivering treatment, etc. are factored out. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for device maintenance of a device or devices per the above, module 24A of some embodiments can, instead or in addition, effect changes in operation of the devices requiring such maintenance, e.g., through signaling of those devices to recalibrate sensors, reset alarms, and so forth, by way of example.

Dialysate Supply

By way of further example, in further embodiments, module 24A can (i) infer from patterns of dialysate flow, dialysate temperature and/or conductivity alerts (and/or sensor data) reflected in information from the devices 10A-10P (raw, analyzed of otherwise) that the devices have a faulty dialysate supply (e.g., a leak in a supply line, an incorrect or empty supply constituent, etc), and (ii) generate reports and/or immediate alerts directing health care providers and/or others at affected treatment centers of a possible need to make such adjustments and/or control the devices 10A-10P to facilitate such adjustment on a per-patient, per-provider or other basis.

Particularly, for example, module 24A can infer from dialysate flow, temperature and/or conductivity alerts signaled (and/or readings taken) by a device, e.g., device 10K during treatment of a single patent in a single treatment session that the device may have a faulty supply, and can generate reports and/or immediate alerts as discussed above in order to alert that health care providers and/or others associated with that treatment center 64F. In the illustrated embodiment, the module 24A makes such an inference whenever the sensors of the treating device, here, 10K, detect even a single conductivity, dialysate flow or temperature alert during a treatment session. In other embodiments, this can be conditioned on detection of multiple such instances during a session. In yet other embodiments, it can be conditioned on detection of such condition or conditions over multiple treatment sessions of the same patient (e.g., detection of two or more conductivity, temperature and/or flow alerts in at least three out of five consecutive treatment sessions for that patient).

In addition to, or instead of, reporting on possible dialysate supply faults, module 24A of some embodiments can, instead or in addition, effect changes in operation of the devices 10K to correct such faults, e.g., through signaling of a suitably equipped such device 10K to use an alternate supply source in connection with treatment of the patient. Typically, such control is effected along with an alert to processor 14 and accompanying display on LCD 16 of device 10K necessitating confirmation of the change by a health care provider via keyboard 18 before it makes further treatment of the patient.

Instead or in addition, module 24A of the embodiment of FIG. 5 can infer, by cross-correlating conductivity, dialysate temperature and/or dialysate flow alerts signaled (and/or readings taken) by one or more devices of a single center (e.g., devices 10K-10M of center 64F) or of multiple centers (e.g., devices 10I-10J, 10K-10M, 10P of centers 64D-64F) with treatment, administrative or other data from those devices and/or center(s), that such devices when operated under the care of a specific device or group of devices and/or of a specific health care provider (e.g., dialysis nurse and/or physician) or group of providers (e.g., personnel of a given center, personnel trained by a specific trainer, and so forth) routinely suffer dialysate supply faults. In the illustrated embodiment, the module 24A makes such an inference whenever the cross-correlations suggest that alert-producing treatments associated with a given such provider (or group) deviate statistically significantly from health care provider, treatment facility or other norms. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for dialysate supply correction, module 24A of some embodiments can, instead or in addition, effect changes in operation of the devices (e.g., 10I-10J, 10K-10M, 10P) to facilitate such correction, e.g., through signaling of those devices to utilize alternate supply sources connection with treatment of patients under the care of a specific health care provider (e.g., dialysis nurse and/or physician) or group of providers. As above, typically such control is effected along with an alert to processors 14 and accompanying displays on LCDs 16 of the respective devices necessitating confirmation of the changes via keyboards 18 before they carry out further treatment of the patient.

While module 24A can infer that devices 10A-10P operated by a given (group of) health care provider(s) routinely require dialysate supply correction, in some embodiments, module 24A can infer from similar data that sensors of one or more devices 10A-10P may be signaling false conductivity, dialysate temperature and/or flow alerts (or other readings). To this end, module 24A can generate reports and/or immediate alerts in order to alert the health care providers and/or others of the possible need for device maintenance in these regards upon drawing such an inference when cross-correlation of alerts signaled (and/or readings taken) by multiple devices of a single center (e.g., devices 10K-10M of center 64F) or of multiple centers (e.g., devices 10I-10J, 10K-10M, 10P of centers 64D-64F) with treatment, administrative or other data from those devices and/or center(s) suggest that a pattern or frequency of conductivity, temperature or flow alerts (or readings) associated with a single such device deviate statistically significantly from those of other devices, e.g., when factors such as patient treated, health care provider delivering treatment, etc. are factored out. In other embodiments, such an inference can be conditioned on such deviation over the course over a specific period, e.g., a week or month. In yet other embodiments, it can be conditioned, instead or in addition, on statistically significant deviation that exceeds a designated threshold of statistical significance, e.g., a designated chi-squared test threshold value, by way of non-limiting example.

In addition to, or instead of, reporting on the possible need for device maintenance of a device or devices per the above, module 24A of some embodiments can, instead or in addition, effect changes in operation of the devices requiring such maintenance, e.g., through signaling of those devices to recalibrate sensors, reset alarms, and so forth, by way of example.

Described herein are systems and methods meeting the objects set forth above, among others. Advantages of the systems and methods are, among others, that they allow care providers to readily monitor and document (or otherwise report on) the patient's treatment and response, providing alerts or other warnings when those are not proceeding as expected. Additional advantages are that the methods and systems provide operations support that can range from generating printed or online reports identifying those causes (e.g., for post-facto assessment by health care providers, administrators and the like seeking to improve the provision and/or efficiency of care delivered by devices 10A-10P) to immediate alerts (e.g., for physicians, nurse or other health care providers or other personnel at the front line of care delivery) to automated device control (e.g., for efficient delivery of care).

It will be appreciated that the embodiments described here are merely examples of the invention and that other embodiments, incorporating modifications on those shown here, fall within the scope of the invention. Thus, by way of non-limiting example, in some embodiments, digital data processor 24 is co-located with device 10, e.g., in a dialysis clinic.

In view of the foregoing, what we claim is:
1. A distributed dialysis care delivery system comprising:
 a) a plurality of dialysis care delivery devices disposed at a plurality of treatment centers, each dialysis care delivery device comprising
  (i) a processor and a storage device;
  (ii) a dialysis treatment apparatus including sensors that sense (a) physiometric characteristics of a respective patient in connection with treatment by the dialysis treatment apparatus, and (b) operating conditions of any of the dialysis care delivery device and the dialysis treatment apparatus, wherein the sensors include one or more of blood pressure sensors, and any of zero, one or more of temperature sensors, pulse sensors, electrochemical sensors, fluid flow sensors, fluid temperature sensors, fluid level sensors, power sensors, maintenance status sensors,
   wherein the processor receives information on the physiometric characteristics of the patient and the operating conditions from the sensors and signals alerts in response to blood pressure readings from the respective sensors and stores the information into the storage device, and (iii) a network interface, wherein the processor coupled with the network interface transmits the physiometric characteristics and operating conditions through the network interface to a remote digital data processing system; and b) the remote digital data processing system comprising i) an analysis module that compares received information on physiometric characteristics and operating conditions received from the plurality of dialysis care delivery devices with any of (a) one another, (b) prior information received from the dialysis care delivery devices and/or from patient records, (c) one or more predetermined values on the physiometric characteristics and the operating conditions, to monitor treatment of patients and operating conditions of the medical treatment apparatus and to identify discrepancies in dialysis treatment at a said treatment center, and ii) a reporting module that generates a report and signals an alert on determining that a said treatment center is not doing as expected, iii) where the analysis module compares received information on physiometric characteristics from the plurality of dialysis care delivery devices with one another to cross-correlate blood pressure alerts respectively signaled by those devices with treatment information from others of those other devices, and iv) wherein the reporting module displays an alarm on determining that a first said patient requires medication adjustment in light of deviation of a said cross-correlation by a designated chi-squared test threshold value over the course of a designated period, and wherein the reporting module effects changes in operation of the dialysis care delivery device of said first patent by making that adjustment.

2. The health care delivery system of claim 1, in which the analysis module (i) linearly infers, from patterns of hypotension reflected in data from the dialysis care delivery device, that patients under care by one or more of said dialysis care delivery devices at a particular treatment center requires a "dry weight" adjustment based on difference of the patterns of hypotension over a specific period.

3. The health care delivery system of claim 1, in which the analysis module (i) linearly infers, from patterns of hypotension reflected in data from the dialysis care delivery device, that patients under care by one or more of said dialysis care delivery devices at a particular treatment center requires a medication adjustment based on difference of the patterns of hypotension over a specific period.

4. The health care delivery system of claim 1, in which the analysis module (i) linearly infers, from patterns of hypotension reflected in data from the dialysis care delivery device, that patients under care by one or more of said dialysis care delivery devices at a particular treatment center requires a filtration rate adjustment based on difference of the patterns of hypotension over a specific period.

5. The health care delivery system of claim 1, in which the analysis module (i) linearly infers, from patterns of hypotension reflected in data from the dialysis care delivery device, that patients under care by one or more of said dialysis care delivery devices at a particular treatment center requires an incoming/fresh dialysate temperature adjustment based on difference of the patterns of hypotension over a specific period.

6. The health care delivery system of claim 1, in which analysis module (i) linearly infers from patterns of hypotension reflected in data from the dialysis care delivery device that patients under care by one or more of said dialysis care delivery devices at a particular treatment center requires a hemocoagulant medication adjustment and/or vascular access evaluation based on difference of the patterns of hypotension over a specific period.

7. The device of claim 1, wherein the reporting module displays the alarm when the alerts generated by the first monitoring logic indicate that the first patient requires anti-coagulation medication adjustment in light of deviation of said cross-correlation by the designated chi-squared test threshold value over the course of designated period.

8. The device of claim 7, wherein a first said dialysis apparatus responds to signaling generated by the reporting module in connection with the alarm by modifying an amount of anticoagulant infused into dialysates in connection with treatment of the first patient by that apparatus.

9. A distributed dialysis care delivery system comprising:

a) a plurality of dialysis care delivery devices disposed at a plurality of treatment centers, each dialysis care delivery device comprising (i) a processor and a storage device;

(ii) a dialysis treatment apparatus including sensors that sense (a) physiometric characteristics of a respective patient in connection with treatment by the dialysis treatment apparatus, and (b) operating conditions of any of the dialysis care delivery device and the dialysis treatment apparatus, wherein the sensors include one or more of blood pressure sensors, and any of zero, one or more of temperature sensors, pulse sensors, electrochemical sensors, fluid flow sensors, fluid temperature sensors, fluid level sensors, power sensors, maintenance status sensors, wherein the processor receives information on the physiometric characteristics of the patient and the operating conditions from the sensors and signals alerts in response to blood pressure readings from the respective sensors and stores the information into the storage device, and (iii) a network interface, wherein the processor coupled with the network interface transmits the physiometric characteristics and operating conditions through the network interface to a remote digital data processing system; and b) the remote digital data processing system comprising i) an analysis module that compares received information on physiometric characteristics and operating conditions received from the plurality of dialysis care delivery devices with any of (a) one another, (b) prior information received from the dialysis care delivery devices and/or from patient records, (c) one or more predetermined values on the physiometric characteristics and the operating conditions, to monitor treatment of patients and operating conditions of the medical treatment apparatus and to identify discrepancies in dialysis treatment at a said treatment center, and ii) a reporting module that generates a report and signals an alert on determining that a said treatment center is not doing as expected, iii) where the analysis module compares received information on physiometric characteristics from the plurality of dialysis care delivery devices with one another to cross-correlate blood pressure alerts respectively signaled by those devices with treatment information from others of those other devices, and iv) wherein the reporting module displays an alarm on determining that a first said patient requires a filtration rate adjustment in light of deviation of a said cross-correlation by a designated chi-squared test threshold value over the course of a designated period, and wherein the reporting module effects changes in operation of the dialysis care delivery device of said first patent by making that adjustment.

10. The device of claim 9, wherein a said first dialysis apparatus responds to signaling generated by the reporting logic in connection with the alarm by modifying a filtration rate in connection with treatment of the first patient by that apparatus.

11. A device, comprising:
A) a first sensor to take blood pressure readings of a first patient in connection with treatment rendered by a first dialysis apparatus,
B) first monitoring logic coupled to the first sensor to signal alerts in response to blood pressure readings from the sensor,
C) a plurality of additional monitoring logics, each coupled to a respective sensor that takes blood pressure readings of a respective additional patient in connection with treatment rendered thereto by a respective additional dialysis apparatus, and each that signals alerts in response to blood pressure readings from the respective sensor,
D) analysis logic in communications coupling with the first monitoring logic and with the plurality of additional monitoring logics to cross-correlate blood pressure alerts signaled by the first monitoring logic for the first patient with blood pressure alerts signaled by the plurality of additional monitoring logics for the additional patients,
E) reporting logic to display an alarm when the alerts generated by the first monitoring logic indicate that the first patient requires medication adjustment in light of deviation of said cross-correlation by a designated chi-squared test threshold value over the course of designated period, and wherein the reporting logic effects changes in operation of the first dialysis apparatus by making that adjustment.

12. The device of claim 11, wherein the reporting logic displays the alarm when the alerts generated by the first monitoring logic indicate that the first patient requires anti-coagulation medication adjustment in light of deviation of said cross-correlation by the designated chi-squared test threshold value over the course of designated period.

13. The device of claim 11, wherein the first dialysis apparatus responds to signaling generated by the reporting logic in connection with the alarm by modifying an amount of anticoagulant infused into dialysates in connection with treatment of the first patient by that apparatus.

14. A device, comprising:
A) a first sensor to take blood pressure readings of a first patient in connection with treatment rendered by a first dialysis apparatus,
B) first monitoring logic coupled to the first sensor to signal alerts in response to blood pressure readings from the sensor,
C) a plurality of additional monitoring logics, each coupled to a respective sensor that takes blood pressure readings of a respective additional patient in connection with treatment rendered thereto by a respective additional dialysis apparatus, and each that signals alerts in response to blood pressure readings from the respective sensor,
D) analysis logic in communications coupling with the first monitoring logic and with the plurality of additional monitoring logics to cross-correlate blood pressure readings signaled by the first monitoring logic for the first patient with blood pressure readings signaled by the plurality of additional monitoring logics for the additional patients,
E) reporting logic to display an alarm when the alerts generated by the first monitoring logic indicate that the first patient requires a filtration rate adjustment in light of deviation of said cross-correlation by a designated chi-squared test threshold value over the course of designated period, and wherein the reporting logic effects changes in operation of the first dialysis apparatus by making that adjustment.

15. The device of claim 14, wherein the first dialysis apparatus responds to signaling generated by the reporting logic in connection with the alarm by modifying a filtration rate in connection with treatment of the first patient by that apparatus.

* * * * *